United States Patent [19]
White

[11] Patent Number: 4,532,336
[45] Date of Patent: Jul. 30, 1985

[54] 6'-ALKYLSPECTINOMYCINS

[75] Inventor: David R. White, Kalamazoo, Mich.

[73] Assignee: The Upjohn Company, Kalamazoo, Mich.

[21] Appl. No.: 449,304

[22] Filed: Dec. 13, 1982

Related U.S. Application Data

[63] Continuation-in-part of Ser. No. 359,723, Mar. 19, 1982, abandoned.

[51] Int. Cl.$^3$ .......... C07D 323/04
[52] U.S. Cl. .......... 549/361
[58] Field of Search .......... 549/361

[56] References Cited

U.S. PATENT DOCUMENTS

| | | | |
|---|---|---|---|
| 3,234,092 | 2/1966 | Bergy et al. | 167/65 |
| 4,173,647 | 11/1979 | Maier et al. | 549/361 |
| 4,282,152 | 8/1981 | White | 549/361 |
| 4,351,771 | 9/1982 | White et al. | 549/361 |
| 4,380,651 | 4/1983 | White | 549/361 |
| 4,405,797 | 9/1983 | Thomas | 549/361 |
| 4,420,623 | 12/1983 | White | 549/361 |
| 4,465,848 | 8/1984 | Thomas et al. | 549/361 |

FOREIGN PATENT DOCUMENTS

| | | | |
|---|---|---|---|
| 2117757 | 10/1983 | United Kingdom | 549/361 |

OTHER PUBLICATIONS

Rosenbrook et al., J. Antibiotics, 28, pp. 953 and 960 (1975), 31, p. 451 (1978).
Carney et al., J. Antibiotics, vol. 30, No. 11, pp. 960–964 (1977).
Foley et al., J. Org. Chem., 43, 22, pp. 4355–4359 (1978).
Lemieux, Can. J. Chem., 51, pp. 53, 19 (1973).
Mallams et al., J. Chem. Soc. Perkin I, pp. 1113–1126 (see p. 1118), pp. 1097–1113 (1976).
Hanessian et al., "Synthesis of (+)-Spectinomycin", Journal of Am. Chem. Society (JACS), vol. 101, No. 19, p. 5839 (1979).

*Primary Examiner*—Ethel G. Love
*Attorney, Agent, or Firm*—Sidney B. Williams, Jr.

[57] ABSTRACT

Process for preparing 6'-alkylspectinomycin and analogs thereof. Also provided are novel intermediates utilized in the process.

18 Claims, No Drawings

6'-ALKYLSPECTINOMYCINS

This application is a continuation-in-part of application Ser. No. 359,723, filed Mar. 19, 1982 and now abandoned.

FIELD OF THE INVENTION

The invention concerns a method for the synthesis of 6'-alkyl spectinomycin and analogs thereof including intermediates utilized in the method. Also claimed are some alkyl spectinomycin analogs that exhibit especially good antibacterial activity.

DESCRIPTION OF THE PRIOR ART

Spectinomycin A is a known antibiotic and was first prepared by a microbiological process. See Bergy et al., U.S. Pat. No. 3,234,092.

Some analogs of spectinomycin are described by Rosenbrook Jr. et al., in J. Antibiotics, 28, pp. 953 and 960 (1975) and J. Antibiotics, 31, p. 451 (1978). In addition, Carney et al. describe chlorodeoxy derivatives of spectinomycin in J. Antibiotics, 30, 960 (1977). Further, 9-epi-4(R)-dihydrospectinomycin is reported by Foley et al., in J. Org. Chem., 43, 22 pp. 4355–4339 (1978). However, biological activity is not reported for any of the spectinomycin analogs and derivatives disclosed in the above-cited references.

Lemieux, Can. J. Chem., 51, p. 53 (1973) teaches a preferential reaction at the 5-hydroxyl of 2-deoxystreptamine (1) with tri-O-acetyl-2-deoxy-2-nitroso-α-D-glycopyranosyl chloride (2) to give a α-pseudodisaccharide wherein CBz is carbobenzyloxy. Mallams et al., J. Chem. Soc. Perkin I, p. 1118 (1976), extend the Lemieux reaction to synthesize di- and tri-saccharides.

Removal of oximes is taught by Lemieux et al., Can. J. Chem. 51, p. 19 (1973) and Mallams et al., J. Chem. Soc. Perkin I, p. 1097 (1976).

Hannessian et al., "Synthesis of (+)-spectinomycin", Journal of Am. Chem. Society (JACS), Vol. 101, No. 19, p. 5839 (1979), describe a chemical synthesis of spectinomycin.

White et al., Tetrahedron Letters, July, 1979, disclose a chemical synthesis of spectinomycin and analogs thereof. The same synthesis is disclosed in Ser. No. 150,530, filed May 26, 1980, now U.S. Pat. No. 4,351,771, which is a continuation of Ser. No. 020,172, filed Mar. 3, 1979, now abandoned. Application Ser. Nos. 285,164, now U.S. Pat. No. 4,380,651 and 285,165, now U.S. Pat. No. 4,380,652, both filed July 20, 1981, disclose methods for preparing 6'-methyl spectinomycin analogs and intermediates utilized in the methods.

U.S. application Ser. No. 312,035 filed Oct. 16, 1981, now U.S. Pat. No. 4,465,848 discloses a process for the demethylation of spectinomycin or its analogs and realkylation of the intermediates and U.S. application Ser. No. 314,261 filed Oct. 23, 1981, now abandoned, discloses spectinomycin analogs wherein modifications have been effected at the 3'-position.

SUMMARY OF THE INVENTION

A dienone is converted to a large variety of 6'-alkylspectinomycin analogs by copper catalyzed Grignard addition. The sequence employs several versatile intermediates. The invention involves modification at C-6' using an enoneacylate.

DETAILED DESCRIPTION OF THE INVENTION

More specifically, this invention relates to a process for preparing compounds of Formula I which involves utilizing an enoneacylate VII as the starting material. The process can be represented and illustrated in the reaction sequence of Scheme I, wherein R is hydrogen or alkyl, R' is alkyl of from 1 to 18 carbon atoms or a cycloalkyl group in which the longest extension of the cyclic system contains 1 to 4 carbon atoms, inclusive. $R_1$ through $R_9$ are selected from the group consisting of hydrogen, lower alkyl, lower alkenyl, and lower alkynyl; $R'_2$, $R'_3$, $R'_6$ and $R'_7$ are selected from the group consisting of lower alkyl, lower alkenyl, lower alkynyl, and a blocking group selected from the group consisting of aralkoxycarbonyl, halogenated alkoxycarbonyl and alkoxycarbonyl; with the proviso that one of $R_2$ and $R_3$ is always hydrogen and one of $R_6$ and $R_7$ is always hydrogen, and the further proviso that one of $R'_2$ and $R'_3$ is always a blocking group and one of $R'_6$ and $R'_7$ is always a blocking group; $R_{10}$ is acyl. A is selected from the group consisting of oxygen and sulfur, and B and $B_1$ are the same or different and are selected from the group consisting of hydrogen, hydroxy, alkoxy, o-lower alkenyl, thio, thio-lower alkyl and thio-lower alkenyl. Some of the intermediates and processes between VI and I are disclosed in Ser. No. 020,073, filed Mar. 13, 1979, and Ser. No. 285,164 filed July 20, 1981.

The numbering of carbons shown in compound I will be used in discussions thereof throughout the specification.

The compounds prepared by the process of this invention include the hydrate forms of compounds of Formula I. These compounds are hydrated at the 3' position and have the Formula I';

wherein A, B, $B_1$, and $R_1$ through $R_{10}$ are the same as defined above. Also included are pharmaceutically acceptable salts of the compounds of formulae I and I'.

"Lower alkyl" means methyl, ethyl, propyl, butyl, pentyl, hexyl, heptyl, octyl, and the isomeric forms thereof.

"Lower alkenyl" means ethenyl, propenyl, butenyl, pentenyl, hexenyl, heptenyl, octenyl and the isomeric forms thereof.

"Lower alkynyl" means ethynyl, propynyl, butynyl, pentynyl, hexynyl, heptynyl, octynyl and the isomeric forms thereof.

"Acyl" means formyl, acetyl, propionyl, butyryl and pentanoyl.

"Halogenated alkoxycarbonyl" means mono-, di-, tri-halomethoxycarbonyl; mono-, di-, tri-haloethoxycarbonyl; mono-, tri-halopropoxycarbonyl; mono-, di-, tri-halobutoxycarbonyl, mono-, di-, tri-halopentoxycarbonyl and isomeric forms thereof.

"Halo" means fluoro, chloro, bromo and iodo.

"Aralkoxycarbonyl" means benzyloxycarbonyl, phenylthoxycarbonyl, phenylpropoxycarbonyl, diphenyloctoxycarbonyl and isomeric forms thereof and fluoroenylmethoxy carbonyl.

"Alkoxycarbonyl" means isopropyloxy carbonyl, tertiary-butyloxy carbonyl, and tertiary-pentyloxycarbonyl.

Alkyl means an alkyl group containing from 1 to 20 carbon atoms both straight chains and branched chains.

It is meant that as used in this description and in the appended claims that when more than one hydroxy or alkoxy is present on the sugar moiety herein they may be the same or different.

The invention also includes novel intermediates II', III and IV. The dienone IV is a highly versatile Michael acceptor; an excellent intermediate for modification.

The term "α-anomer" means a 1' substituent below the plane of the ring system and the term "β-anomer" means that anomers having the C-1' configuration corresponding to spectinomycin.

Compounds prepared by the process of this invention which exhibit desirable biological activity are β-anomers of compound I. This glycosidic configuration is found in spectinomycin shown in Chart 1.

In Step 1, enoneacylate VII is reacted with dimethylformamide dimethyl acetal in a solvent to yield the enamine VI. The temperature range of the reaction is generally 25° C. to reflux, preferably 40° C. to 80°. Time of the reaction may range from 1 hr. to 48 hrs., preferably 2 hrs. to 10 hrs. Dimethylformamide dimethylacetal is used in excess. The preferred reaction time and solvent are 7 hrs. and dimethylformamide. Other acetals of dimethylformamide such as di-t-butyl can also be used.

The starting enoneacetate and methods for preparing it are described in U.S. application Ser. No. 150,530 filed May 16, 1980.

The enamine can be isolated from the mixture by conventional procedures such as extraction, chromatography and combinations thereof.

In Step 2 side chain reduction of the enamine VI is effectuated under standard cyanoborohydride conditions to yield amine V. The amine can be isolated from the reaction mixture by conventional means such as extraction, chromatography and combinations thereof.

Step 3 involves reacting amine V with an alkyl halide in the presence of a solvent to yield dienone IV. The reaction can be conducted at a temperature of about 0° to about 100°, for a time period of about 1 hr. to about 30 hrs., and using an excess of methyl iodide. The preferred reaction temperature and times are 20° C. to 40° C., 1 hr. to 20 hrs. Solvents that can be used include methylene chloride, $CHCl_3$, THF, and ether. The preferred solvent is methylene chloride.

An alternate and preferred method for conducting step 3 involves reacting amine V with meta chloroperbenzoic acid in a solvent to yield dienone IV. The reaction can be conducted at a temperature of about −20° to 50°, for a time period of about 1 min. to about 60 min. The preferred reaction temperatures and times are 20° C. to 30° C., and 5 min. to 20 min. Solvents that can be used include etnhyl acetate/Skellysolve B, tetrahydrofuran, dioxan, and $CH_2Cl_2$. The preferred solvent is ethyl acetate/Skellysolve B.

In Step 4, dienone IV is reacted with Grignard reagent in the presence of a copper catalyst to yield III. This reaction is conducted with a solvent at a temperature of about −130 to 0 for a period of about 1 min. to 2 hours. The preferred temperature and reaction time ranges are −78° to −50° and 1 min. to 10 min., respectively. Solvents that may be used include diethylether, 1,2-dimethylethane, tetrahydrofuran and diisopropylether. The preferred solvent is tetrahydrofuran.

In Step 5, enone III is subjected to reduction to yield blocked 6'-alkylspectinomycin II. This is a very critical step in the process for several reasons. It is very difficult to reduce the 4',5' double bond without reducing the 3' carbonyl. Palladium catalysts, i.e. 10% palladium on barium sulfate (ionic palladium, brown catalyst), can be used with partial success, as described above, but the blocking groups, especially carbobenzyloxy groups, are removed so the separation problem is made more difficult. Furthermore, palladium catalysts do not work well on analogs with more highly substituted sugar side chains. Therefore, platinum oxide in the presence of a solvent and a base is preferred.

A second major advantage is that the protecting groups remain so that products can be purified by chromatography before using one of several deprotecting methods. The reaction is conducted by dissolving enone III in the solvent, adding the base, platinum oxide and then contacting the mixture with hydrogen. The reduction is conducted at a temperature of from about 20° to 40°, for a period of about 1 hr. to 4 hrs. Preferred temperature and reaction times are 20° C. to and 40° C. and 2 hrs. to 3 hrs., respectively.

An alternative and preferred method for conducting step 5 involves reducing didehydrospectinomycin III to the protected 6'-spectinomycin II by reacting it with Li-selectride®, a solution of lithium tri-sec-butylborohydride. The reaction is conducted by dissolving didehydrospectinomycin III in a solvent, adding the lithium solution and then base and water. The reduction is conducted at a temperature of from about 100° to −10° for 5 min. to 40 min. Preferred temperatures and reaction times are −78°, −10°, and 5 min. to 60 min., respectively. Solvents that can be used include tetrahydrofuran, dioxane, 1,2-dimethoxyethane and diethylether. The preferred solvent is tetrahydrofuran.

In Step 6 the compound of Formula II is deprotected to yield the compound of Formula I. The particular conditions of deprotection depends upon the particular groups, i.e. group $R'_2$ or $R'_3$ and $R'_6$ or $R'_7$ that block the amine on the actinamine ring. Where that group is benzyloxy carbonyl or aralkoxy carbonyl the deprotection can be conducted under from −10 psi to +200 psi of hydrogen over a conventional catalyst such as palladium black, palladium on carbon, palladium on barium sulfate, or palladium on barium carbonate, while suspended in a solvent, for example, isopropanol, absolute ethanol, methanol ethyl acetate, toluene or tetrahydrofuran. In situ generation of hydrogen from formic acid in methanol is sometimes preferred.

Alternatively, deblocking of compounds wherein $R'_2$, $R'_3$ and $R'_6$ or $R'_7$ are alkoxycarbonyl or aryloxycarbonyl can be conducted in the presence of an acid in solvent such as nitromethane and methylene chloride.

When $R'_2$ or $R'_3$ and $R'_6$ or $R'_7$ are haloalkoxycarbonyl, the deblocking is preferably conducted in the presence of zinc.

A particularly effective process for preparing the compound of Formula VI is depicted by the schematic outline in Scheme II.

Step 1 involves reacting N,N'-dibenzyloxycarbonyl spectinomycin (*JACS* 85, 2652, 1963) with formic acid in the presence of acetic acid annhydride ethylacetate and pyridine. The reaction is conducted at a temperature of about −70° to 10° for a period of about ½ to 30 hours in the presence of a solvent. The preferred temperature range is about −40° to 0° and the preferred reaction time is about 10 to 18 hours. Solvents that can be used include ethyl acetate, tetrahydrofuran, methylene chloride, chloroform and 1,2-dimethylethane. The preferred solvent is ethyl acetate. Step 1 yields a compound of Formula IX.

In Step 2, the compound of Formula IX is reacted with acetic acid annhydride and base to yield a compound of Formula VIII. The reaction is conducted in the absence or the presence of a solvent, at a temperature of about 20° to 90°, and preferably 50° to 70° for a period of time of about 2 to 30 hours, preferably 10 to 20 hours. Solvents that may be used include ethyl acetate, tetrahydrofuran, 1,2-dimethyloxyethane and chloroform. The preferred solvent is ethyl acetate.

In Step 3, compound VIII is subjected to treatment with light in the presence of dibromodimethyl hydantoin to generate a $C_3$ carbonyl in the form of a compound of Formula VII. The reaction is conducted at a temperature of about 10° to 100°, preferably 40° to 80° and a reaction time of 2 to 60 min., preferably 10 to 20 minutes. This step also generates unsaturation at the 4,5-positions.

In Step 4, the compound of Formula VII is reacted with dimethylformamide acetyl in the presence of dimethylformamide, and the product reacted with methanol or water to yield a compound of Formula VI. Step 4 is conducted at a temperature of about 30° to 90°, preferably 40° to 70°, and for a time of about 2 to 6, preferably 3 to 5 hours. Each of the products prepared in the above steps can be removed from the reaction mixture by conventional methods.

Any method within the skill in the art may be used for isolation of an analog or asteric mixture of a compound having Formula I and methods disclosed herein are not meant to be limiting. If isolation is conducted under anhydrous conditions, compounds having a carbonyl group at the 3′ position (Formula I) are obtained. If conducted under aqueous conditions, compounds hydrated at the 3′ position (Formula I′) may be obtained, with the exclusion of compounds VII and VI, which do not hydrate.

The crude analogs may be purified by adsorption on a column of a weakly acidic ion exchange resin such as Amberlite IRC-50 or CG-50 followed by elution with a solvent such as water, methanol, ethanol, ether, tetrahydrofuran, 1,2-dimethoxy ethane or p-dioxane containing hydrochloric acid, hydrobromic acid, hydroiodic acid and sulfuric acid.

Acid salts can be made by neutralizing compounds of Formula I with the appropriate acid to below about pH 7.0 and advantageously to about pH 2 to pH 3. Suitable acids for this purpose include hydrochloric, sulfuric, phosphoric, sulfamic, hydrobromic. and the like. Acid and base salts of the compounds can be used for the same biological purposes as the parent compound.

The compounds of Formula I inhibit the growth of microorganisms in various environments. For example, Formula I conpounds having the $\beta$ configuration are active against *Escherichia coli* and can be used to reduce, arrest, and eradicate slime production in papermill systems caused by its antibacterial action against this microorganism. These $\beta$ anomers also can be used to prolong the life of cultures of *Trichomonas foetus, Trichomonas hominis,* and *Trichomonas vaginalis* by freeing them of *Escherichia coli* contamination. Still further, $\beta$-anomers are active against *Bacillus subtilis* so it can be used to minimize or prevent odor in fish or fish crates caused by this organism. Also, the $\beta$-anomers can be used to swab laboratory benches and equipment in a mycological laboratory. $\beta$-anomers are also effective against *Klebsiella pneumoniae.*

The compounds of Formula I are also effective for treating bacterial infections, such as gonorrhea in mammals, including humans.

Compounds that show corresponding good antibacterial activity are compounds of Formula I wherein R′ is an alkyl group, straight, cyclic, or branch chain system, in which the longest extension of the branch or cyclic system contains from 1 to 4 carbon atoms, inclusive; Examples of R′ include ethyl, propyl, isopropyl, butyl, t-butyl and cyclohexyl. The compounds 6′-n-propylspectinomycin, 6′-n-butylspectinomycin and 6′-pentylspectinomycin are particularly potent antibacterial agents.

The compositions of the present invention are presented for administration to humans and animals in unit dosage forms, such as sterile parenteral solutions or suspensions, eye drops and water-in-oil emulsions containing suitable quantities of the compound of Formula I.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspension can be prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The term "unit dosage form" as used in the specification refers to physically discrete units suitable as unitary dosages for human subjects and animals, each unit containing a predetermined quantity of active material calculated to produce the desired therapeutic effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention. Examples of suitable unit dosage forms in accord with this invention are ampoules, vials, aerosols with metered discharges, segregated multiples of any of the foregoing, and other forms as herein described.

An effective quantity of the compound is employed in treatment. The dosage of the compound for treatment depends on many factors that are well known to those skilled in the art. They include for example, the route of administration and the potency of the particular compound. A dosage schedule for humans of from about 2 to about 4000 mg of compound in a single dose, administered parenterally or in the compositions of this invention, are effective for bacterial infections. More specifically, the single dose is from 5 mg to about 200 mg of compound.

The following described preparations of analogs of spectinomycin and intermediates useful in the preparation thereof are indicative of the scope of this invention and are not to be construed as limitative. Those skilled in the art will promptly recognize variations from the procedures both in the analogs and analog precursors within the novel compounds described as well as reaction conditions and techniques of the invention process.

For example, for each of the Preparations and Examples in the following descriptions, corresponding stereoisomers for each named compound is contemplated to be within the scope of the invention.

PREPARATION 1

N,N'-dibenzyloxycarbonyl-2,6-di-O-formylspectinomycin

A 5 l flask, fitted with a stirrer and thermometer, is charged with ethyl acetate (1.33 l) and 97% formic acid (255 ml). Acetic anhydride (618 ml) is added, with dry ice/acetone cooling, so the temperature stays below −40° C. Pyridine (1.09 l) is slowly added so the temperature is about −40° C. N,N'-dibenzyloxyspectinomycin (100 g) is added and the cooling bath is allowed to come to room temperature with stirring being continued overnight. The solution is diluted with ethyl acetate (1.65 l), washed with 0.5N hydrochloric acid (5×675 ml), water (2×675 ml), 10% aq. sodium bicarbonate (2×675 ml) and brine (2×175 ml). Drying and concentration of the organic layer gives 105 g of N,N'-dibenzyloxycarbonyl-2,6-di-O-formylspectinomycin.

CMR ($d_6$-acetone): 201.6, 161.4, 161.0, 157.1, 13.6, 129.1, 128.4, 128.1, 97.1, 92.1, 73.7, 71.7, 68.3, 67.7, 67.6, 65.9, 56.1, ppm.

Utilizing a procedure similar to Preparation 6 but substituting the appropriately-substituted N,N'-dibenzyloxyspectinomycin for N,N'-dibenzyloxyspectinomycin, there are obtained the di-O-formylspectinomycins of Tables I and II.

TABLE I

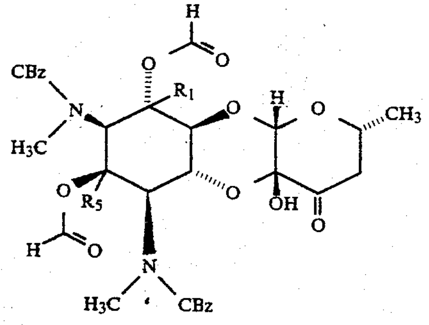

| R1 | R5 |
|---|---|
| $CH_3$— | $CH_3$— |
| $C_2H_5$— | $C_2H_5$— |
| $C_3H_7$— | $C_3H_7$— |
| $C_4H_9$— | $C_4H_9$— |
| $C_5H_{11}$— | $C_5H_{11}$— |
| $C_8H_{11}$— | $C_8H_{11}$— |
| $CH_2$=CH— | $CH_2$=CH— |
| CH≡C— | CH≡C— |

TABLE II

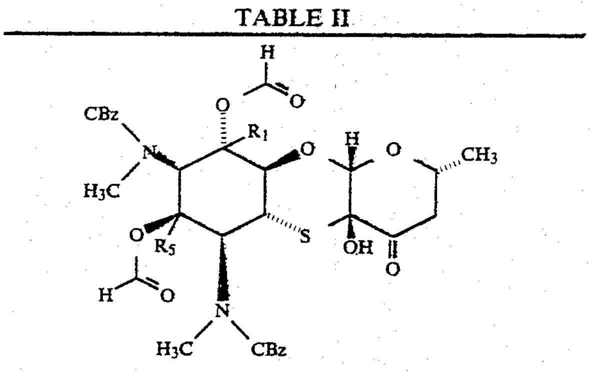

| R1 | R5 |
|---|---|
| $CH_3$— | $CH_3$— |
| $C_2H_5$— | $C_2H_5$— |
| $C_3H_7$— | $C_3H_7$— |
| $C_4H_9$— | $C_4H_9$— |
| $C_5H_{11}$— | $C_5H_{11}$— |
| $C_8H_{11}$— | $C_8H_{11}$— |
| $CH_2$=CH— | $CH_2$=CH— |
| CH≡C— | CH≡C— |

PREPARATION 2

N,N'-dibenzyloxycarbonyl-2,6-di-O-formyl-2'-O-acetylspectinomycin enol acetate

N,N'-dibenzyloxycarbonyl-2,6-di-O-formylspectinomycin (7.0 g), acetic anhydride (15.0 ml), pyridine (30.0 ml), dimethyl aminopyridine (0.5 g) are added to ethyl acetate (50 ml) in a 250 ml flask and heated at 55° overnight. The reaction mixture is diluted with ethyl acetate (500 ml) and hexane (500 ml) and extracted with 0.6 hydrochloric acid (3×1 l), (1×0.5 l) then saturated sodium bicarbonate (2×500 ml) and brine (2×500 ml). The organics are dried over sodium sulfate and concentrated to 7.0 g of N,N'-dibenzyloxycarbonyl-2,6-di-O-formyl-2'-O-acetylspectinomycin enol acetate.

CMR ($d_6$-acetone): 168.9, 167.7, 161.4, 161.0, 157.1, 139.9, 137.8, 129.1, 128.4, 128.2, 128.1, 122.8, 94.7, 92.2, 74.1, 71.3, 69.1, 67.6, 67.2, 56.3, 55.5, 31.4, 30.7, 21.1, 21.0, 20.7 ppm.

Utilizing a procedure similar to Preparation 2, but substituting the appropriately-substituted 2,6-di-O-formyl-2'-O-acetylspectinomycin for N,N'-dicarbobenzyloxycarbonyl 2,6-di-O-formylspectinomycin, there are obtained the enamines of Tables III and IV.

TABLE III

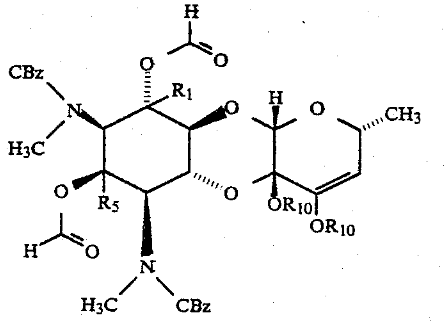

| $R_1$ | $R_5$ | $R_{10}$ |
|---|---|---|
| $CH_3$— | $CH_3$— | $\overset{\overset{O}{\|}}{CH_3C}$— |

TABLE III-continued

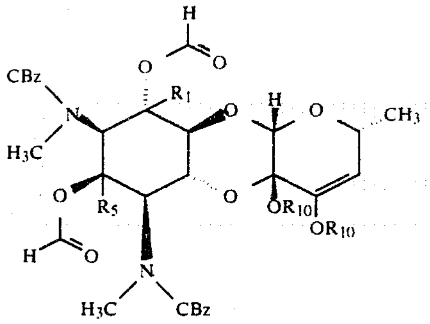

| $R_1$ | $R_5$ | $R_{10}$ |
|---|---|---|
| $C_2H_5-$ | $C_2H_5-$ | $CH_3\overset{\overset{O}{\|}}{C}-$ |
| $n\text{-}C_3H_7-$ | $n\text{-}C_3H_7-$ | $CH_3\overset{\overset{O}{\|}}{C}-$ |
| $n\text{-}C_4H_9-$ | $n\text{-}C_4H_9-$ | $CH_3\overset{\overset{O}{\|}}{C}-$ |
| $n\text{-}C_8H_{17}-$ | $n\text{-}C_8H_{17}-$ | $CH_3\overset{\overset{O}{\|}}{C}-$ |
| $CH_2{=}CH{=}$ | $CH_2{=}CH-$ | $CH_3\overset{\overset{O}{\|}}{C}-$ |
| $CH{\equiv}C-$ | $CH{\equiv}C-$ | $CH_3\overset{\overset{O}{\|}}{C}-$ |
| H— | H— | $CH_3\overset{\overset{O}{\|}}{C}-$ |
| H— | H— | $CH_3\overset{\overset{O}{\|}}{C}-$ |
| H— | H— | $CH_3CH_2\overset{\overset{O}{\|}}{C}-$ |
| H— | H— | $CH_3(CH_2)_2\overset{\overset{O}{\|}}{C}-$ |
| H— | H— | $CH_3(CH_2)_2\overset{\overset{O}{\|}}{C}-$ |
| H— | H— | $CH_3(CH_2)_2\overset{\overset{O}{\|}}{C}-$ |
| H— | H— | $CH_3(CH_2)_2\overset{\overset{O}{\|}}{C}-$ |
| H— | H— | $CH_3(CH_2)_3\overset{\overset{O}{\|}}{C}-$ |
| H— | H— | isopropionyl |
| H— | H— | sec-butyryl |
| H— | H— | t-butyryl |

TABLE IV

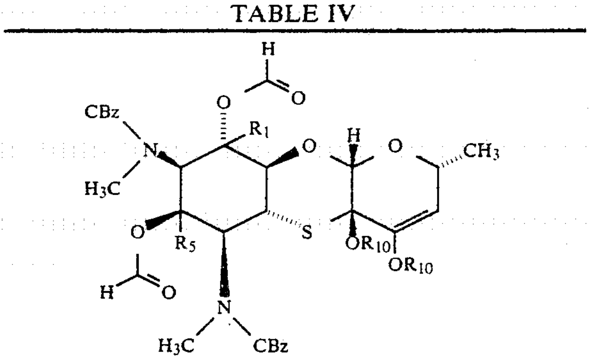

| $R_1$ | $R_5$ | $R_{10}$ |
|---|---|---|
| $CH_3-$ | $CH_3-$ | $CH_3\overset{\overset{O}{\|}}{C}-$ |
| $C_2H_5-$ | $C_2H_5-$ | $CH_3\overset{\overset{O}{\|}}{C}-$ |
| $n\text{-}C_3H_7-$ | $n\text{-}C_3H_7-$ | $CH_3\overset{\overset{O}{\|}}{C}-$ |
| $n\text{-}C_4H_9-$ | $n\text{-}C_4H_9-$ | $CH_3\overset{\overset{O}{\|}}{C}-$ |
| $n\text{-}C_8H_{17}-$ | $n\text{-}C_8H_{17}-$ | $CH_3\overset{\overset{O}{\|}}{C}-$ |
| $CH_2{=}CH{=}$ | $CH_2{=}CH-$ | $CH_3\overset{\overset{O}{\|}}{C}-$ |
| $CH{\equiv}C-$ | $CH{\equiv}C-$ | $CH_3\overset{\overset{O}{\|}}{C}-$ |
| H— | H— | $CH_3\overset{\overset{O}{\|}}{C}-$ |
| H— | H— | $CH_3\overset{\overset{O}{\|}}{C}-$ |
| H— | H— | $CH_3CH_2\overset{\overset{O}{\|}}{C}-$ |
| H— | H— | $CH_3(CH_2)_2\overset{\overset{O}{\|}}{C}-$ |
| H— | H— | $CH_3(CH_2)_2\overset{\overset{O}{\|}}{C}-$ |
| H— | H— | $CH_3(CH_2)_2\overset{\overset{O}{\|}}{C}-$ |
| H— | H— | $CH_3(CH_2)_2\overset{\overset{O}{\|}}{C}-$ |
| H— | H— | $CH_3(CH_2)_3\overset{\overset{O}{\|}}{C}-$ |
| H— | H— | isopropionyl |
| H— | H— | sec-butyryl |
| H— | H— | t-butyryl |

PREPARATION 3

N,N'-dibenzyloxycarbonyl-2,6-di-O-formyl-2'-O-acetyl-4',5'-didehydrospectinomycin N,N'-dibenzyloxycarbonyl-2,6-di-O-formyl-2'-O-acetylspectinomycin enol acetate (5.26 g) is dissolved in carbon tetrachloride (75 ml) and dibromodimethylhydantoin (1.05 g) is added. The solution was brought to reflux under visible light as initiator. After 20 minutes, the solution is cooled, diluted with chloroform (200 ml) and water (100 ml). Phases are separated and organics are washed with aqueous sodium chloride (60 ml). The organics are dried over sodium sulfate and concentrated to give 5.65 g of N,N'-dibenzyloxycarbonyl-2,6-di-O-formyl-2'-O-acetyl-4'-,5'-didehydrospectinomycin.

CMR ($d_6$-acetone): 182.4, 173.4, 170.0, 161.6, 161.0, 157.0, 137.6, 129.2, 128.6, 128.2, 103.4, 95.7, 93.1, 73.7, 72.1, 67.8, 66.9, 56.1, 55.7, 31.8, 30.6, 21.0 ppm.

Utilizing a procedure similar to Preparation 3, but substituting the appropriately-substituted enol acetate for N,N'-dicarbobenzyloxycarbonyl-2,6-di-O-formylacetylspectinomycin, there are obtained the 4',5'-didehydrospectinomycins of Tables V and VI.

TABLE V

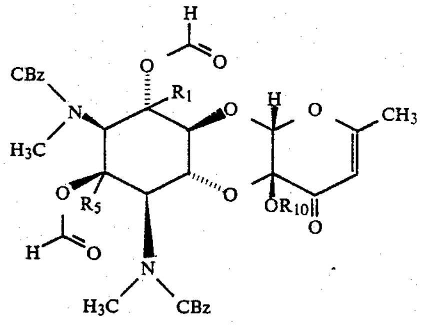

| $R_1$ | $R_5$ | $R_{10}$ |
|---|---|---|
| $CH_3$— | $CH_3$— | $CH_3\overset{O}{\overset{\|}{C}}$— |
| $C_2H_5$— | $C_2H_5$— | $CH_3\overset{O}{\overset{\|}{C}}$— |
| n-$C_3H_7$— | n-$C_3H_7$— | $CH_3\overset{O}{\overset{\|}{C}}$— |
| n-$C_4H_9$— | n-$C_4H_9$— | $CH_3\overset{O}{\overset{\|}{C}}$— |
| n-$C_8H_{17}$— | n-$C_8H_{17}$— | $CH_3\overset{O}{\overset{\|}{C}}$— |
| $CH_2$=CH= | $CH_2$=CH— | $CH_3\overset{O}{\overset{\|}{C}}$— |
| CH≡C— | CH≡C— | $CH_3\overset{O}{\overset{\|}{C}}$— |
| H— | H— | $CH_3\overset{O}{\overset{\|}{C}}$— |
| H— | H— | $CH_3\overset{O}{\overset{\|}{C}}$— |

TABLE V-continued

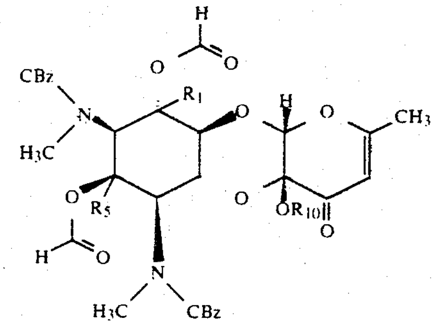

| $R_1$ | $R_5$ | $R_{10}$ |
|---|---|---|
| H— | H— | $CH_3CH_2\overset{O}{\overset{\|}{C}}$— |
| H— | H— | $CH_3(CH_2)_2\overset{O}{\overset{\|}{C}}$— |
| H— | H— | $CH_3(CH_2)_2\overset{O}{\overset{\|}{C}}$— |
| H— | H— | $CH_3(CH_2)_2\overset{O}{\overset{\|}{C}}$— |
| H— | H— | $CH_3(CH_2)_2\overset{O}{\overset{\|}{C}}$— |
| H— | H— | $CH_3(CH_2)_3\overset{O}{\overset{\|}{C}}$— |
| H— | H— | isopropionyl |
| H— | H— | sec-butyryl |
| H— | H— | t-butyryl |

TABLE VI

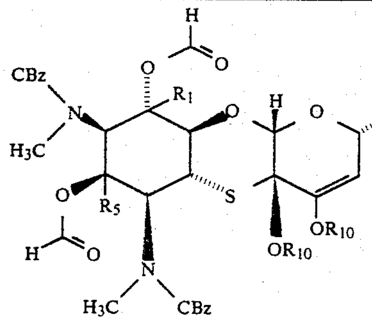

| $R_1$ | $R_5$ | $R_{10}$ |
|---|---|---|
| $CH_3$— | $CH_3$— | $CH_3CO$— |
| $C_2H_5$— | $C_2H_5$— | $CH_3CO$— |
| n-$C_3H_7$— | n-$C_3H_7$— | $CH_3CO$— |
| n-$C_4H_9$— | n-$C_4H_9$— | $CH_3CO$— |
| n-$C_8H_{17}$— | n-$C_8H_{17}$— | $CH_3CO$— |
| $CH_2$=CH= | $CH_2$=CH— | $CH_3CO$— |
| CH≡C— | CH≡C— | $CH_3CO$— |
| H— | H— | $CH_3CO$— |
| H— | H— | $CH_3CO$— |
| H— | H— | $CH_3CH_2CO$— |
| H— | H— | $CH_3(CH_2)_2CO$— |
| H— | H— | $CH_3(CH_2)_2CO$— |
| H | H— | $CH_3(CH_2)_2CO$— |
| H— | H— | $CH_3(CH_2)_2CO$— |
| H— | H— | $CH_3(CH_2)_3CO$— |
| H— | H— | isopropionyl |

TABLE VI-continued

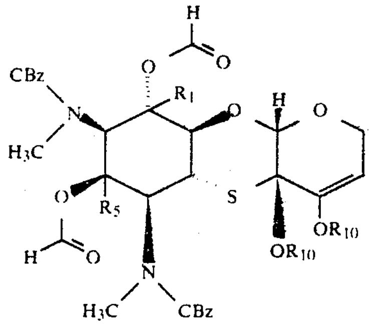

| $R_1$ | $R_5$ | $R_{10}$ |
|---|---|---|
| H— | H— | sec-butyryl |
| H— | H— | t-butyryl |

PREPARATION 4

N,N'-dicarbobenzyloxy-2'-O-acetyl-6-[(dimethyl-amino)methylene]-',5'-didehydrospectinomycin A solution of N,N'-dicarbobenzyloxy-2'-O-acetyl-4',5'-didehydrospectinomycin (22.00 g, 34.4 mmole) and dimethylformamide dimethylacetal (100 ml) in dimethylformamide (100 ml) is stirred for 7 hours at 50°-55° C. with drierite protection. The brown solution is concentrated under vacuum and the residue chromatographed on silica gel (250 g) which has been wet packed in a 2 liter sintered glass funnel. The mixture is eluted with 5% acetonitrile in chloroform (2 liters), 7% (3 liters), 33% (3 liters), 50% (6 liters) over a period of 1½ hours. Half liter fractions are taken. The fractions are evaluated by TLC (1/1 acetonitrile in chloroform) and combined to give 19.78 g of pure N,N-dicarbobenzyloxy-2'-O-acetyl-6-[(dimethyl-amino)methylene]-4',5'-didehydrospectinomycin and 3.30 g of N,N-dicarbobenzyloxy-2'-O-acetyl-6-[(dimethyl-amino)-methylene]-4',5'-didehydrospectinomycin containing some DMF (dimethyl formamide). The latter fraction was rechromatographed as above (but using 60 g of silica gel) to give 2.75 g of pure N,N-dicarbobenzyloxy-2'-O-acetyl-6-[(dimethyl-amino)-methylene]-4',5'-didehydrospectinomycin. Total yield is 22.53 g (94% yield).

CD($CH_3OH$)$[\theta]_{311}$nm—10,400±1,200, $[\theta]_{285}$—2,500±1,200, $[\theta]_{246}$—1,200±1,200.

IR(mull): 3380, 1750, 1695, 1675sh, 1600, 1555, 1500, 1385, 1350, 1280, 1240, 1195, 1185, 1145, 1110, 1085, 1065, 1025, 1000, 960, 770, 740, 645 $cm^{-1}$.

PMR ($CDCl_3$): 2.13 (3H, s), 2.82 (3H, s), 2.89 (6H, br.s), 2.91 (3H, s), 5.10 (4H, br.s), 5.16 (1H, s), 5.97 (1H, s), 7.30δ (10H, s).

CMR ($CD_3COCD_3$): 20.9, 31.2, 31.5, 30-44 br, 36.3, 59.6, 66.2, 67.3, 74.6, 75.4, 88.7, 94.9, 95.0, 95.1, 95.5, 128.3, 129.1, 137.9, 138.0, 150.3, 157.2, 157.7, 163.3, 169.8, 171.2, 180.3 PPM.

Mass spectrum, m/c (diTMS): 839 (M+), 824, 797, 779, 730, 688. Peak matched calcd: 839.3480; Found: 839.3466.

Utilizing procedures similar to Preparation 4, but substituting the appropriately-substituted enone acetate for N,N'-dicarbobenzyloxy-2'-O-acetyl-4',5'-didehydrospectinomycin, there are obtained the enamines of Tables VII and VIII.

TABLE VII

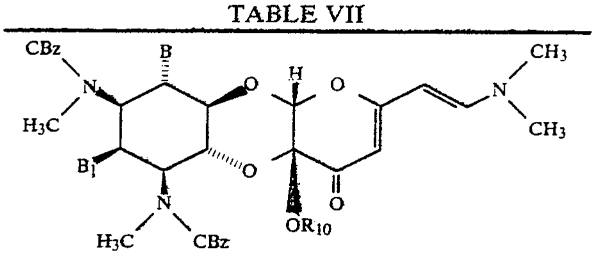

| B | $B_1$ | $R_{10}$ |
|---|---|---|
| HO— | HO— | $CH_3\overset{O}{\overset{\|}{C}}-$ |
| $CH_3O$— | HO— | $CH_3\overset{O}{\overset{\|}{C}}-$ |
| $C_2H_5O$— | HO— | $CH_3\overset{O}{\overset{\|}{C}}-$ |
| HS— | HO— | $CH_3\overset{O}{\overset{\|}{C}}-$ |
| $CH_3S$— | HO— | $CH_3\overset{O}{\overset{\|}{C}}-$ |
| $C_2H_5S$— | HO— | $CH_3\overset{O}{\overset{\|}{C}}-$ |
| H— | HO— | $CH_3\overset{O}{\overset{\|}{C}}-$ |
| HO— | H— | $CH_3\overset{O}{\overset{\|}{C}}-$ |
| HO— | $CH_3O$— | $CH_3\overset{O}{\overset{\|}{C}}-$ |
| HO— | $C_2H_5O$— | $CH_3\overset{O}{\overset{\|}{C}}-$ |
| HO— | HS— | $CH_3\overset{O}{\overset{\|}{C}}-$ |
| HO— | $CH_3S$— | $CH_3\overset{O}{\overset{\|}{C}}-$ |
| HO— | $C_2H_5S$— | $CH_3CH_2\overset{O}{\overset{\|}{C}}-$ |
| HO— | HO— | $CH_3(CH_2)_2\overset{O}{\overset{\|}{C}}-$ |
| HO— | HO— | $CH_3(CH_2)_2\overset{O}{\overset{\|}{C}}-$ |
| HO— | HO— | $CH_3(CH_2)_2\overset{O}{\overset{\|}{C}}-$ |
| HO— | HO— | $CH_3(CH_2)_2\overset{O}{\overset{\|}{C}}-$ |
| HO— | HO— | $CH_3(CH_2)_3-\overset{O}{\overset{\|}{C}}-$ |

TABLE VII-continued

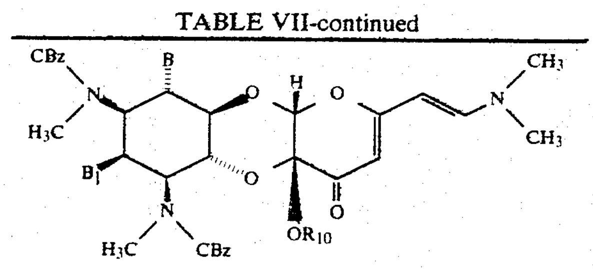

| B | $B_1$ | $R_{10}$ |
|---|---|---|
| HO— | HO— | isopropionyl |
| HO— | HO— | sec-butyryl |
| HO— | HO— | t-butyryl |

TABLE VIII

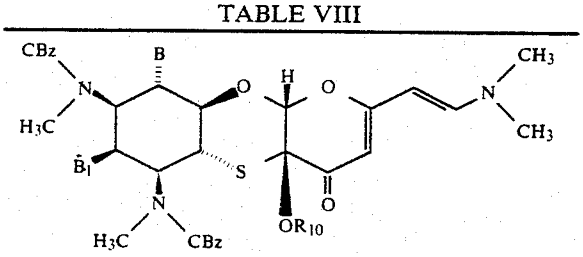

| B | $B_1$ | $R_{10}$ |
|---|---|---|
| HO— | HO— | $CH_3\overset{O}{\overset{\|}{C}}-$ |
| $CH_3O$— | HO— | $CH_3\overset{O}{\overset{\|}{C}}-$ |
| $C_2H_5O$— | HO— | $CH_3\overset{O}{\overset{\|}{C}}-$ |
| HS— | HO— | $CH_3\overset{O}{\overset{\|}{C}}-$ |
| $CH_3S$— | HO— | $CH_3\overset{O}{\overset{\|}{C}}-$ |
| $C_2H_5S$— | HO— | $CH_3\overset{O}{\overset{\|}{C}}-$ |
| H— | HO— | $CH_3\overset{O}{\overset{\|}{C}}-$ |
| HO— | H— | $CH_3\overset{O}{\overset{\|}{C}}-$ |
| HO— | $CH_3O$— | $CH_3\overset{O}{\overset{\|}{C}}-$ |
| HO— | $C_2H_5O$— | $CH_3\overset{O}{\overset{\|}{C}}-$ |
| HO— | H— | $CH_3\overset{O}{\overset{\|}{C}}-$ |
| HO— | $CH_3S$— | $CH_3\overset{O}{\overset{\|}{C}}-$ |

TABLE VIII-continued

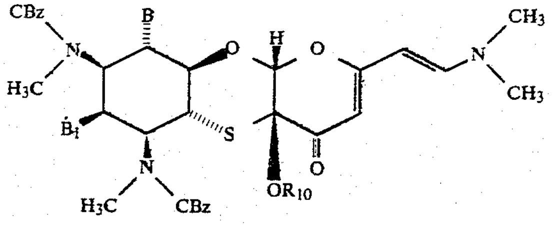

| B | $B_1$ | $R_{10}$ |
|---|---|---|
| HO— | $C_2H_5S$— | $CH_2CH_2\overset{O}{\overset{\|}{C}}-$ |
| HO— | HO— | $CH_2CH_2\overset{O}{\overset{\|}{C}}-$ |
| HO— | HO— | $CH_3(CH_2)_2\overset{O}{\overset{\|}{C}}-$ |
| HO— | HO— | $CH_3(CH_2)_2\overset{O}{\overset{\|}{C}}-$ |
| HO— | HO— | $CH_3(CH_2)_3\overset{O}{\overset{\|}{C}}-$ |
| HO— | HO— | $CH_3(CH_2)_3-\overset{O}{\overset{\|}{C}}-$ |
| HO— | HO— | isopropionyl |
| HO— | HO— | sec-butyryl |
| HO— | HO— | t-butyryl |

PREPARATION 5

N,N'-dicarbobenzyloxy-2'-O-acetyl-6[(dimethylamino)-methylene]-4',5'-didehydrospectinomycin N,N'-dibenzyloxycarbonyl-2,6-di-O-formyl-2'-O-acetyl-4',5'didehydrospectinomycin (5.50 g) is dissolved in dimethylformamide (39.0 ml) and dimethylformamide dimethyl acetyl acetal (36.0 ml) is added. After heating at 55°–60° for 4 hours, methanol (36 ml) is added and heating at 55°–60° continued for 3 hours. The residue is taken up in chloroform (15 ml) and applied to silica gel (200 ml) in a filter. The product is washed off after the remaining DMF by elution with chloroform (½ l), 5% acetonitrile in chloroform (0.8 l), 30% acetonitrile in chloroform (150 ml) and acetonitrile (1 l). Fractions. are combined to give 2.71 g of N,N'-dicarbobenzyloxy-2'-O-acetyl-6-[(dimethylamino-methylene]-4',5'-didehydrospectinomycin.

CMR ($d_6$-acetone): 180.3, 171.2, 169.8, 157.0, 150.3, 137.9, 129.0, 128.2, 95.5, 95.2, 95.1, 94.8, 88.7, 75.3, 67.3, 66.2, 59.9, 56.7, 41.0, 31.4, 30.7, 21.2 ppm.

Utilizing a procedure similar to Preparation 5, but substituting the appropriately substituted 4',5'-didehydrospectinomycin for N,N'-dibenzyloxycarbonyl-2,6-di-O-formyl-2'-O-acetyl-4',5'-didehydrospectinomycin, there are obtained the enamines of Tables IX and X.

TABLE IX

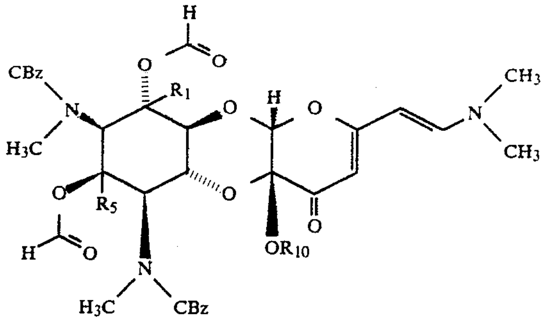

| $R_1$ | $R_5$ | $R_{10}$ |
|---|---|---|
| $CH_3$— | $CH_3$— | $CH_3\overset{O}{\overset{\|}{C}}$— |
| $C_2H_5$— | $C_2H_5$— | $CH_3\overset{O}{\overset{\|}{C}}$— |
| n-$C_3H_7$— | n-$C_3H_7$— | $CH_3\overset{O}{\overset{\|}{C}}$— |
| n-$C_4H_9$— | n-$C_4H_9$— | $CH_3\overset{O}{\overset{\|}{C}}$— |
| n-$C_8H_{17}$— | n-$C_8H_{17}$— | $CH_3\overset{O}{\overset{\|}{C}}$— |
| $CH_2$=CH= | $CH_2$=CH— | $CH_3\overset{O}{\overset{\|}{C}}$— |
| CH≡C— | CH≡C— | $CH_3\overset{O}{\overset{\|}{C}}$— |
| H— | H— | $CH_3\overset{O}{\overset{\|}{C}}$— |
| H— | H— | $CH_3\overset{O}{\overset{\|}{C}}$— |
| H— | H— | $CH_3CH_2\overset{O}{\overset{\|}{C}}$— |
| H— | H— | $CH_3(CH_2)_2\overset{O}{\overset{\|}{C}}$— |
| H— | H— | $CH_3(CH_2)_2\overset{O}{\overset{\|}{C}}$— |
| H— | H— | $CH_3(CH_2)_2\overset{O}{\overset{\|}{C}}$— |
| H— | H— | $CH_3(CH_2)_2\overset{O}{\overset{\|}{C}}$— |
| H— | H— | $CH_3(CH_2)_3\overset{O}{\overset{\|}{C}}$— |
| H— | H— | isopropionyl |
| H— | H— | sec-butyryl |
| H— | H— | t-butyryl |

TABLE X

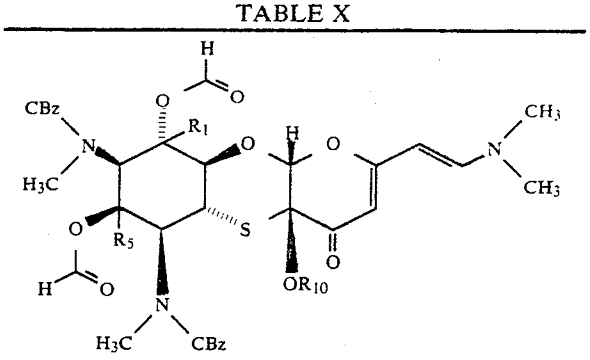

| $R_1$ | $R_5$ | $R_{10}$ |
|---|---|---|
| $CH_3$— | $CH_3$— | $CH_3\overset{O}{\overset{\|}{C}}$— |
| $C_2H_5$— | $C_2H_5$— | $CH_3\overset{O}{\overset{\|}{C}}$— |
| n-$C_3H_7$— | n-$C_3H_7$— | $CH_3\overset{O}{\overset{\|}{C}}$— |
| n-$C_4H_9$— | n-$C_4H_9$— | $CH_3\overset{O}{\overset{\|}{C}}$— |
| n-$C_8H_{17}$— | n-$C_8H_{17}$— | $CH_3\overset{O}{\overset{\|}{C}}$— |
| $CH_2$=CH= | $CH_2$=CH— | $CH_3\overset{O}{\overset{\|}{C}}$— |
| CH≡C— | CH≡C— | $CH_3\overset{O}{\overset{\|}{C}}$— |
| H— | H— | $CH_3\overset{O}{\overset{\|}{C}}$— |
| H— | H— | $CH_3\overset{O}{\overset{\|}{C}}$— |
| H— | H— | $CH_3CH_2\overset{O}{\overset{\|}{C}}$— |
| H— | H— | $CH_3(CH_2)_2\overset{O}{\overset{\|}{C}}$— |
| H— | H— | $CH_3(CH_2)_2\overset{O}{\overset{\|}{C}}$— |
| H— | H— | $CH_3(CH_2)_2\overset{O}{\overset{\|}{C}}$— |
| H— | H— | $CH_3(CH_2)_2\overset{O}{\overset{\|}{C}}$— |
| H— | H— | $CH_3(CH_2)_3\overset{O}{\overset{\|}{C}}$— |
| H— | H— | isopropionyl |
| H— | H— | sec-butyryl |
| H— | H— | t-butyryl |

PREPARATION 6

N,N'-dicarbobenzyloxy-2-O'-acetyl-6'-(dimethylaminomethyl)-4',5'-didehydrospectinomycin N,N'-dicarbobenzyloxy-2'-O-acety-6'-[(dimethylamino)methylene]-4',5'-didehydrospectinomycin (20.00 g, 28.78 mmole) and methyl orange (5 mg) are dissolved in methanol (200 ml). The pH is adjusted to 4 with 2N methanolic hydrogen chloride and sodium cyanoborohydride is added to portions over 20 minutes with frequent readjustment to pH using 2N methanolic hydrogen chloride. After a total of 2.00 g (31.83 mmole) of sodium cyanoborohydride has been added, the solution is stirred an additional hour at room temperature; TLC (1:9 methanol/chloroform) shows starting material has been consumed. The solution is concentrated, diluted with ethyl acetate (500 ml), 0.1N sodium hydroxide (250 ml), 1.0N NaOH (25 ml) and saturated brine (250 ml). The organic phase is washed with brine (200 ml+100 ml). The three aqueous phases are washed in sequence with ethyl acetate (2×200 ml). Organic extracts are dried over sodium sulfate and concentrated to yield N,N'-dicarbobenzyloxy-2-O'-acetyl-6'-dimethylaminomethyl)-4',5'-didehydrospectinomycin as a foam (17.93 g, 89% yield).

CD ($CH_3OH$): $[\theta]_{321}$—12,000±1,100, $[\theta]_{270}$±1,100.

UV ($C_2H_5OH$): 273 nm (8,800), 377 nm(sh) (63).

PMR ($CDCl_3$): 2.13 (3h, s), 2.17 (6H, s), 2.46 (3H, s), 3.05 (3H, s), 3.06 (3H, s), 5.05 (4H, d), 5.34 (1H, s), 5.89 (1H, s), 7.26 (10H, d).

CMR ($CD_3COCD_3$): 20.9, 31.3, 45., 56.1, 57.1, 61.3, 66.1, 67.3, 74.0, 75.4, 93.7, 96.0, 103.1, 128.3, 129.1, 137.9, 157.2, 170.0, 174.9, 183.1 ppm.

PREPARATION 6a

N,N'-dicarbobenzyloxy-2,'O-acetyl-6'-(dimethylaminomethyl)-4',5'-didehydrospectinomycin N,N'-dicarbobenzyloxy-2'-O-acetyl-6'-[(dimethylamino)methylene]4',5'-didehydrospectinomycin (57.0 g, 78.7 mmole) ethyl acetate (450 ml) and methanol (105 ml) are mixed. The pH is adjusted to 4, with 2N hydrochloric acid and sodium cyanoborohydride (7.3 g) added in five portions over five minutes with frequent readjustment to pH of 4 using 2N hydrochloric acid. After completion of addition of sodium cyanoborohydride the pH is held at 4 for an additional 15 minutes. TLC (1:9 methanol/chloroform) shows starting material has been consumed. The solution is then mixed with water (350 ml) in sodium hydroxide (175) and the phases separated. The upper phase is exhausted with brine (250 ml) and Skellysolve B (150 ml) added to break the emulsion. The two aqueous phases are backwashed in sequence with ethyl acetate (300 ml) plus Skellysolve B (75 ml) and the total organics are dried over sodium sulfate. The sodium sulfate is filtered to yield a filtrate containing N,N'-dicarbobenzyloxy-2,'O-acetyl-6'-(dimethylaminomethyl)-4',5'-didehydrospectinomycin.

Using procedures similar to those of Preparation 6 and 6a but substituting the appropriately substituted precursor enamines from Tables I and II for the N,N'-dicarbobenzyloxy-2'-O-acetyl-6'-[(dimethylamino)methylene]-4',5'-didehydrospectinomycin, there is obtained the protected spectinomycin analogs of Tables XI and XII.

TABLE XI

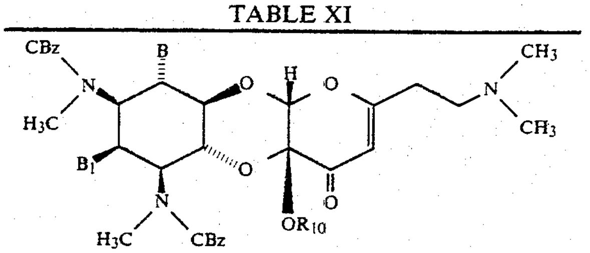

| B | $B_1$ | $R_{10}$ |
|---|---|---|
| HO— | HO— | $CH_3C(=O)-$ |
| $CH_3O-$ | HO— | $CH_3C(=O)-$ |
| $C_2H_5O-$ | HO— | $CH_3C(=O)-$ |
| HS— | HO— | $CH_3C(=O)-$ |
| $CH_3S-$ | HO— | $CH_3C(=O)-$ |
| $C_2H_5S-$ | HO— | $CH_3C(=O)-$ |
| H— | HO— | $CH_3C(=O)-$ |
| HO— | H— | $CH_3C(=O)-$ |
| HO— | $CH_3O-$ | $CH_3C(=O)-$ |
| HO— | $C_2H_5O-$ | $CH_3C(=O)-$ |
| HO— | HS— | $CH_3C(=O)-$ |
| HO— | $CH_3S-$ | $CH_3C(=O)-$ |
| HO— | $C_2H_5S-$ | $CH_3CH_2C(=O)-$ |
| HO— | HO— | $CH_2CH_2C(=O)-$ |
| HO— | HO— | $CH_3(CH_2)_2C(=O)-$ |
| HO— | HO— | $CH_3(CH_2)_2C(=O)-$ |
| HO— | HO— | $CH_3(CH_2)_2C(=O)-$ |
| HO— | HO— | $CH_3(CH_2)_3-C(=O)-$ |

TABLE XI-continued

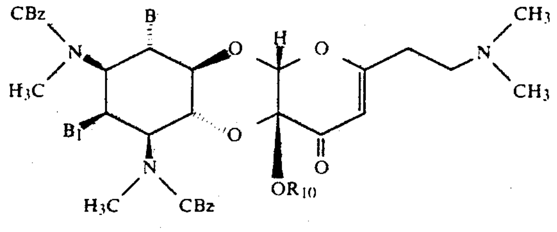

| B | $B_1$ | $R_{10}$ |
|---|---|---|
| HO— | HO— | isopropionyl |
| HO— | HO— | sec-butyryl |
| HO— | HO— | t-butyryl |

TABLE XII

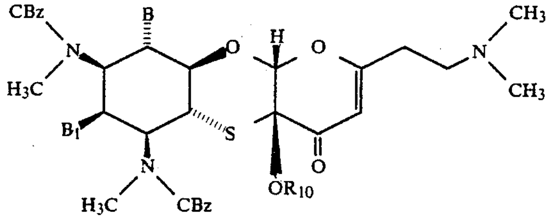

| B | $B_1$ | $R_{10}$ |
|---|---|---|
| HO— | HO— | $CH_3\overset{\overset{O}{\|}}{C}-$ |
| $CH_3O-$ | HO— | $CH_3\overset{\overset{O}{\|}}{C}-$ |
| $C_2H_5O-$ | HO— | $CH_3\overset{\overset{O}{\|}}{C}-$ |
| HS— | HO— | $CH_3\overset{\overset{O}{\|}}{C}-$ |
| $CH_3S-$ | HO— | $CH_3\overset{\overset{O}{\|}}{C}-$ |
| $C_2H_5S-$ | HO— | $CH_3\overset{\overset{O}{\|}}{C}-$ |
| H— | HO— | $CH_3\overset{\overset{O}{\|}}{C}-$ |
| HO— | H— | $CH_3\overset{\overset{O}{\|}}{C}-$ |
| HO— | $CH_3O-$ | $CH_3\overset{\overset{O}{\|}}{C}-$ |
| HO— | $C_2H_5O-$ | $CH_3\overset{\overset{O}{\|}}{C}-$ |
| HO— | HS— | $CH_3\overset{\overset{O}{\|}}{C}-$ |
| HO— | $CH_3S-$ | $CH_3\overset{\overset{O}{\|}}{C}-$ |

TABLE XII-continued

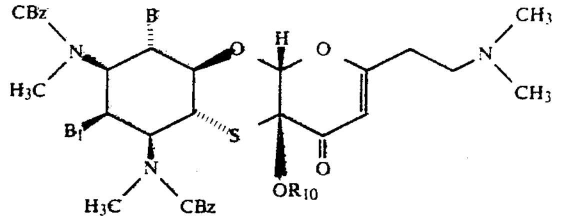

| B | $B_1$ | $R_{10}$ |
|---|---|---|
| HO— | $C_2H_5S-$ | $CH_3CH_2\overset{\overset{O}{\|}}{C}-$ |
| HO— | HO— | $CH_3CH_2\overset{\overset{O}{\|}}{C}-$ |
| HO— | HO— | $CH_3(CH_2)_2\overset{\overset{O}{\|}}{C}-$ |
| HO— | HO— | $CH_3(CH_2)_2\overset{\overset{O}{\|}}{C}-$ |
| HO— | HO— | $CH_2(CH_2)_3\overset{\overset{O}{\|}}{C}-$ |
| HO— | HO— | $CH_3(CH_2)_3-\overset{\overset{O}{\|}}{C}-$ |
| HO— | HO— | isopropionyl |
| HO— | HO— | sec-butyryl |
| HO— | HO— | t-butyryl |

PREPARATION 7

N,N'-dicarbobenzyloxy-2-O'-acetyl-6'-methylene-4',5'-didehydrospectinomycin

N,N'-dicarbobenzyloxy-2-O'-acetyl-6'-(dimethylaminomethyl)-4',5'-didehydrospectinomycin (17.43 g, 25.00 mmole) is dissolved in methylene chloride (200 ml) and methyl iodide (18.0 ml, 41.04 g, 289 mmole) and stirred at room temperature for 6 hours. After standing at 10° C. for an additional 16 hours the solution is concentrated and then dissolved in 1/9 acetonitrile/chloroform. The mixture is chromatographed on silica gel (300 g) using the same solvent (4 liters), then 1/3 acetonitrile/chloroform (4 liters). The first pure substance eluted is obtained by combining fractions and concentrating to yield 10.03 g of N,N'-dicarbobenzyloxy-2-O'-acetyl-6'-methylene-4',5'-didehydrospectinomycin (61% yield).

CD ($CH_3OH$): $[\theta]_{334}$—26,100±2,300, $[\theta]_{240}$—44,800±2,300, $[\theta]_{244}$nm—10,800±2.300.

UV ($C_2H_5OH$): 204sh (22.500), 241 (6,750) 250sh (5,900), 256sh (4,900), 293 nm (14,650).

PMR ($CDCl_3$): 2.13 (3H, s), 3.03 (3H, s), 3.06 (3H, s), 5.05 (4H, d), 5.44 (1H, s), 5.61 (1H, q), 5.95 (1H, s), 6.11 (1H, s), 6.19 (1H, s), 7.29 pp (10H, s).

CMR ($CD_3COCD_3$): 20.9, 31.4, 57.2, 60.1, 66.2, 67.4, 74.1, 74.7, 75.6, 94.0, 96.1, 104.3, 125.3, 128.4, 129.2, 131.1, 138.0, 138.1, 157.6, 166.6, 170.2, 184.0 ppm.

PREPARATION 7a

N,N'-dicarbobenzyloxy-2-O'-acetyl-6'-methylene-4',5'-didehydrospectinomycin

To the N,N'-dicarbobenzyloxy-2,'O-acetyl-6'-(dimethylaminomethyl)-4',5'-didehydrospectinomycin in ethyl acetate/Skellysolve B prepared in Preparation 6a is added m-chloroperbenzoic acid (15 g). After stirring the solution for 10 minutes saturated sodium bicarbonate (300 ml) is added with mixing and the phases separated. The organic layer is washed with brine (250 ml) and then methanol is added to break the emulsion. The two aqueous fractions are washed in sequence with ethyl acetate (250 ml) and Skellysolve B (75 ml). The organics are combined, dried with sodium sulfate and then concentrated to a solid. The solid is dissolved in chloroform and the solution chromatographed on silica (1 liter wet packed in a 1 liter sintered glass funnel) using chloroform (4 liter), 2% acetonitrile/chloroform (2 liters), 5% acetonitrile/chloroform (2 liters), 10% acetonitrile (4 liters) and 15% acetonitrile (4 liters). Fractions 10–14 are combined and concentrated to yield 15.7 g of a mixture containing N,N'-dicarbobenzyloxy-2-O'-acetyl-6'-methylene-4',5'-didehydrospectinomycin.

Using procedures similar to those of Preparation 7 and 7a but substituting the appropriately substituted didehydrospectinomycin for N,N'-dicarbobenzyloxy-2-O'-acetyl-6'-(dimethylaminomethyl)-4',5'-didehydrospectinomycin, there is obtained the protected spectinomycin analogs of Tables XIII and XIV.

TABLE XIII

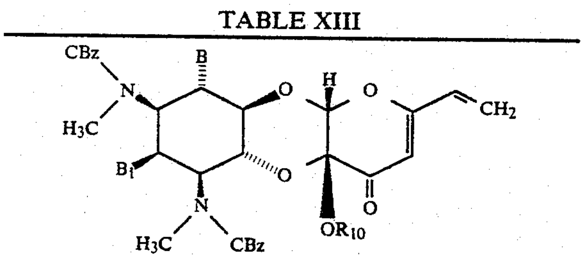

| B | $B_1$ | $R_{10}$ |
|---|---|---|
| HO— | HO— | $CH_3\overset{O}{\overset{\|}{C}}-$ |
| $CH_3O-$ | HO— | $CH_3\overset{O}{\overset{\|}{C}}-$ |
| $C_2H_5O-$ | HO— | $CH_3\overset{O}{\overset{\|}{C}}-$ |
| HS— | HO— | $CH_3\overset{O}{\overset{\|}{C}}-$ |
| $CH_3S-$ | HO— | $CH_3\overset{O}{\overset{\|}{C}}-$ |
| $C_2H_5S-$ | HO— | $CH_3\overset{O}{\overset{\|}{C}}-$ |
| H— | HO— | $CH_3\overset{O}{\overset{\|}{C}}-$ |
| HO— | H— | $CH_3\overset{O}{\overset{\|}{C}}-$ |

TABLE XIII-continued

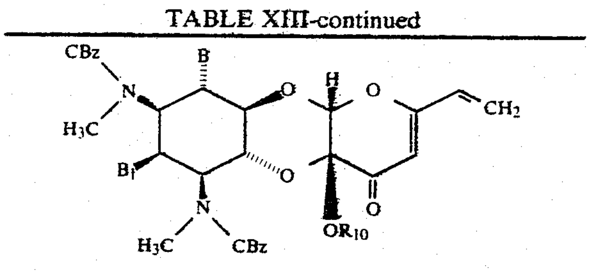

| B | $B_1$ | $R_{10}$ |
|---|---|---|
| HO— | $CH_3O-$ | $CH_3\overset{O}{\overset{\|}{C}}-$ |
| HO— | $C_2H_5O-$ | $CH_3\overset{O}{\overset{\|}{C}}-$ |
| HO— | H— | $CH_3\overset{O}{\overset{\|}{C}}-$ |
| HO— | $CH_2S-$ | $CH_3\overset{O}{\overset{\|}{C}}-$ |
| HO— | $C_2H_5S-$ | $CH_2CH_2\overset{O}{\overset{\|}{C}}-$ |
| HO— | HO— | $CH_2CH_2\overset{O}{\overset{\|}{C}}-$ |
| HO— | HO— | $CH_2(CH_2)_2\overset{O}{\overset{\|}{C}}-$ |
| HO— | HO— | $CH_3(CH_2)_2\overset{O}{\overset{\|}{C}}-$ |
| HO— | HO— | $CH_3(CH_2)_3\overset{O}{\overset{\|}{C}}-$ |
| HO— | HO— | $CH_3(CH_2)_3-\overset{O}{\overset{\|}{C}}-$ |
| HO— | HO— | isopropionyl |
| HO— | HO— | sec-butyryl |
| HO— | HO— | t-butyryl |

TABLE XIV

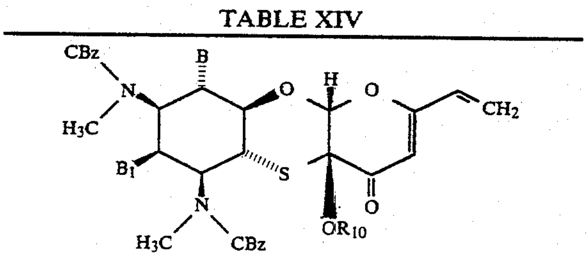

| B | $B_1$ | $R_{10}$ |
|---|---|---|
| HO— | HO— | $CH_3\overset{O}{\overset{\|}{C}}-$ |
| $CH_3O-$ | HO— | $CH_3\overset{O}{\overset{\|}{C}}-$ |

TABLE XIV-continued

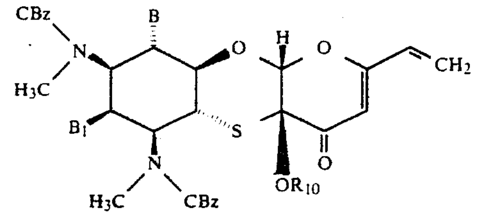

| B | $B_1$ | $R_{10}$ |
|---|---|---|
| $C_2H_5O-$ | $HO-$ | $CH_3\overset{O}{\overset{\|}{C}}-$ |
| $HS-$ | $HO-$ | $CH_3\overset{O}{\overset{\|}{C}}-$ |
| $CH_3S-$ | $HO-$ | $CH_3\overset{O}{\overset{\|}{C}}-$ |
| $C_2H_5S-$ | $HO-$ | $CH_3\overset{O}{\overset{\|}{C}}-$ |
| $H-$ | $HO-$ | $CH_3\overset{O}{\overset{\|}{C}}-$ |
| $HO-$ | $H-$ | $CH_3\overset{O}{\overset{\|}{C}}-$ |
| $HO-$ | $CH_3O-$ | $CH_3\overset{O}{\overset{\|}{C}}-$ |
| $HO-$ | $C_2H_5O-$ | $CH_3\overset{O}{\overset{\|}{C}}-$ |
| $HO-$ | $HS-$ | $CH_3\overset{O}{\overset{\|}{C}}-$ |
| $HO-$ | $CH_3S-$ | $CH_3\overset{O}{\overset{\|}{C}}-$ |
| $HO-$ | $C_2H_5S-$ | $CH_3CH_2\overset{O}{\overset{\|}{C}}-$ |
| $HO-$ | $HO-$ | $CH_3CH_2\overset{O}{\overset{\|}{C}}-$ |
| $HO-$ | $HO-$ | $CH_3(CH_2)_2\overset{O}{\overset{\|}{C}}-$ |
| $HO-$ | $HO-$ | $CH_3(CH_2)_2\overset{O}{\overset{\|}{C}}-$ |
| $HO-$ | $HO-$ | $CH_3(CH_2)_3\overset{O}{\overset{\|}{C}}-$ |
| $HO-$ | $HO-$ | $CH_3(CH_2)_3-\overset{O}{\overset{\|}{C}}-$ |
| $HO-$ | $HO-$ | isopropionyl |
| $HO-$ | $HO-$ | sec-butyryl |
| $HO-$ | $HO-$ | t-butyryl |

PREPARATION 8

N,N'-dibenzyloxycarbonyl-2'-O-acetyl-4',5'-didehydro-6'-n-octylspectinomycin

A dried 15 ml three neck flask is equipped with a magnetic stir bar and a serum cap. N,N'-dicarbobenzyloxy-2-O'-acetyl-6'-methylene-4,5'-didehydrospectinomycin (332 mg, 0.5 mmole) is dissolved in tetrahydrofuran (10 ml) and cupric bromide (25 mg) is added. After cooling the slurry to −78° under a nitrogen atmosphere, heptylmagnesium bromide (1.2 ml, 2.1M) is added by injection through the serum cap. A TLC probe (1:4 $CH_3CH$:$CHCl_3$) shows starting material has been converted to a slightly less polar major product. The reaction mixture is poured onto a solution of ethyl acetate (20 ml) and acetic acid (0.3 ml). After dilution with water (10 ml) and mixing, the organic phase is separated and washed with saturated sodium bicarbonate (15 ml) and saturated brine (10 ml). The aqueous extracts are, in turn, washed with ethyl acetate (20 ml). Organic extracts are dried over sodium sulfate and concentrated to a foam. Chromatography on 6.0 g silica in 1:9 acetonitrile-chloroform gives (0.32 g) purified N,N'-dibenzyloxycarbonyl-2'-O-acetyl-4',5'-didehydro-6'-n-octylspectinomycin.

CMR ($CD_3COCD_3$): 183.1, 178.4, 170.0, 157.7, 138.0, 124.1, 128.3, 102.5, 96.0, 93.8, 75.6, 73.4, 67.3, 66.1, 59.7, 57.2, 35.0, 32.4, 31.4, 30.0, 29.8, 29.6, 26.7, 23.2, 20.4, 14.3 ppm.

Mass spectrum (silylated): M/e 856 ($M^+$), 841, 769, 671, 600, 484, 356, 313, 284, 243, 217, 199, 171, 145, 73.

Utilizing a procedure similar to that used in Preparation 8 but substituting the appropriately substituted alkyl magnesium bromide for heptyl magnesium bromide there is obtained N,N'-dibenzyloxycarbonyl-2'-O-acetyl-4',5'-didehydro-6'-ethylspectinomycin.

CMR 183.1, 176.2, 170.0, 151.3, 137.81, 129.0, 128.1, 102.6, 95.9, 93.6, 75.3, 74.2, 67.3, 66.1, 60.0, 57.1, 36.8, 31.3, 20.8, 20.0, 13.6 ppm.

N,N'-dibenzyloxycarbonyl-2'-O-acetyl-4',5'-didehydro-6'-n-propylspectinomycin.

CMR 183.3, 176.5, 170.1, 157.2, 138.2, 129.2, 128.4, 102.6, 96.1, 93.8, 75.6, 74.6, 67.4, 66.2, 60.1, 57.3, 34.8, 32.2, 28.8, 22.7, 20.9, 13.9 ppm.

N,N'-dibenzyloxycarbonyl-2'-O-acetyl-4',5'-didehydro-6'-n-butylyspectinomycin.

CMR 183.1, 176.4, 170.0, 157.9, 138.2, 129.1, 128.7, 102.5, 96.0, 93.8, 75.6, 74.6, 67.3, 66.1, 60.0, 57.2, 35.0, 31.7, 31.4, 26.3, 22.8, 20.9, 14.1 ppm.

N,N'-dibenzyloxycarbonyl-2'-O-acetyl-4',5'-didehydro-6'-n-pentylspectinomycin.

CMR 183.1, 176.5, 170.0, 157.8, 138.4, 129.1, 128.3, 102.6, 96.0, 93.7, 75.6, 74.8, 67.3, 66.0, 60.2, 57.1, 35.0, 32.0, 31.4, 29.2, 26.6, 23.0, 20.9, 14.2 ppm.

and the N,N-dibenzyloxycarbonyl-2'-O-acetyl-4',5'-didehydro-6'-n-octyl-spectinomycin analogs of Tables XV and XVI.

TABLE XV

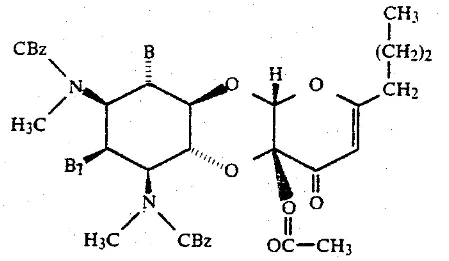

| B | $B_1$ |
|---|---|
| HO— | HO— |
| $CH_3O$— | HO— |
| $C_2H_5O$— | HO— |
| HS— | HO— |
| $CH_3S$— | HO— |
| $C_2H_5S$— | HO— |
| H— | HO— |
| HO— | H— |
| HO— | $CH_3O$— |
| HO— | $C_2H_5O$— |
| HO— | HS— |
| HO— | $CH_3S$— |
| HO— | $C_2H_5S$— |
| HO— | HO— |
| HO— | HO— |
| HO— | HO— |
| HO— | HO— |
| HO— | HO— |
| HO— | HO— |
| HO— | HO— |
| HO— | HO— |

TABLE XVI

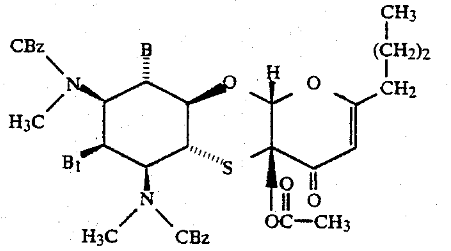

| B | $B_1$ |
|---|---|
| HO— | HO— |
| $CH_3O$— | HO— |
| $C_2H_5O$— | HO— |
| HS— | HO— |
| $CH_3S$— | HO— |
| $C_2H_5S$— | HO— |
| H— | HO— |
| HO— | H— |
| HO— | $CH_3O$— |
| HO— | $C_2H_5$— |
| HO— | $H_2$— |
| HO— | $CH_3S$— |
| HO— | $C_2H_5S$— |
| HO— | HO— |
| HO— | HO— |
| HO— | HO— |
| HO— | HO— |
| HO— | HO— |
| HO— | HO— |
| HO— | HO— |
| HO— | HO— |

PREPARATION 9

N,N'-dibenzyloxycarbonyl-6'-octylspectinomycin

N,N'-dicarbobenzyloxy-2'-O-acetyl-4',5'-didehydro-6'-n-octylspectinomycin (0.32 g) is dissolved in 2-propanol (12.0 ml) and triethylamine (0.12 ml) is added. The solution is divided into four equal parts and placed in test tubes each containing 30 mg of platinum oxide. The test tubes are placed in a Parr bottle carefully and allowed to shake at 20 pounds per square inch (psi) of hydrogen for 2 hours. The catalyst is filtered and water (0.7 ml) is added to the combined filtrates. After standing 16 hours the filtrate is heated an additional ¾ hours at 65°, concentrated and chromatographed on silica (6 g). N,N'-dibenzyloxycarbonyl-6'-n-octylspectinomycin is eluted with ½% methanol chloroform (200 ml), 1% (100 ml), 1½% (150 ml), 2% (200 ml) and 3% (100 ml). The desired fractions are found by TLC analysis; the product gives a purple spot when sprayed with DNP spray, then sulfuric acid spray and heated. Weight of product is 0.09 g.

CMR ($CD_3COCD_3$): 201.5, 157, 138.1, 129.1, 128.3, 97.5, 92.3, 75.1, 74.7, 74.6, 71.8, 67.2, 66.4, 65.6, 61.1, 60.1, 57.5, 44.1, 36.1, 32.4, 31.7, 31.4, 30.7, 30.1, 29.8, 25.7, 23.1, 14.3 ppm.

Mass Spectrum (silylated): M/e=928 (M+), 913, 901, 837, 823, 793, 745, 624, 611, 539, 493, 449, 359, 91.

PREPARATION 9a

N,N'-dibenzyloxycarbonyl-6'-propylspectinomycin

A solution of 4',5'-didehydro-2-O-acetyl-N,N'-dibenzyloxycarbonyl-6'-propylspectinomycin (0.70 g) is dissolved in tetrahydrofuran (10 ml) and cooled to −78°. A 1M solution of lithium tri-sec-butylborohydride in tetrahydrofuran (3.0 ml) is added. After stirring under nitrogen for 25 min. at −78° the solution is poured into ethyl acetate (10 ml) plus acetic acd (0.2 ml). More ethyl acetate (10 ml), water (1.0 ml) and triethylamine (1.0 ml) are added. After two hours additional triethylamine (1.0 ml) is added and the solution is stirred at room temperature for 16 hours. Skellysolve B (20 ml) and sodium bicarbonate (saturated aqueous solution 15 ml) are added and phases are separated. The upper phase is washed with aqueous saturated NaCl (15 ml). The organic phase is dried over sodium sulfate and concentrated to an oil. This is chromatographed on silica gel (40 ml), packed in methylene chloride. The product is eluted with methylene chloride (50 ml), 1:1 methylene chloride/chloroform (60 ml), chloroform (50 ml), ½% methanol in chloroform (100 ml), 1% methanol in chloroform (100 ml), 2½% methanol in chloroform (100 ml), 5% methanol in chloroform (200 ml). Concentration of appropriate fractions gives 0.45 g (68.3%) of N,N'-dibenzyloxycarbonyl-6'-propylspectinomycin.

Utilizing procedures similar to those used in Preparations 9 or 9a but substituting the appropriately substituted N,N'-dicarbobenzyloxy-6'-alkylspectinomycin analog for N,N-dicarbobenzyloxy-6'-octylspectinomycin there is obtained N,N'-dibenzyloxycarbonyl-6'-ethylspectinomycin.

CMR 201.0, 158.2, 138.2, 129.1, 128.4, 97.6, 92.3, 75.2, 74.7, 74.6, 71.5, 67.2, 66.2, 65.6, 61.1, 60.2, 57.6, 57.3, 44.1, 38.2, 31.7, 31.4, 18.2, 14.1 ppm.

N,N'-dibenzyloxycarbonyl-6'-n-propylspectinomycin.

CMR 201.8, 156.7, 138.1, 129.1, 128.3, 97.5, 92.3, 75.1, 74.7, 74.6, 71.8, 67.2, 66.4, 65.6, 60.9, 59.9, 57.5, 44.1, 35.7, 31.4, 30.8, 27.7, 23.0, 14.2 ppm.

N,N'-dibenzyloxycarbonyl-6'-n-butylspectinomycin.

CMR 201.5, 156.2, 138.2, 129.4, 128.6, 97.7, 92.6, 75.3, 75.1, 74.8, 72.1, 67.6, 66.7, 66.0, 61.0, 60.0, 57.8, 44.3, 35.3, 31.6, 32.5, 32.1, 31.8, 31.2, 30.2, 29.2, 25.6, 23.3, 14.6 ppm.

N,N'-dibenzyloxycarbonyl-6'-isobutylspectinomycin.

N,N'-dibenzyloxycarbonyl-6'-n-pentylspectinomycin.

CMR 202.0, 158.1, 138.2, 129.1, 128.4, 97.6, 92.4, 75.2, 74.6, 74.0, 71.8, 67.2, 66.4, 65.7, 61.1, 60.1, 57.5, 57.3, 44.1, 36.1, 32.3, 31.7, 31.4, 29.7, 25.6, 23.2, 14.3 ppm.

N,N'-dibenzyloxycarbonyl-6'-(3,3-dimethyl)-n-butylspectinomycin.

N,N'-dibenzyloxycarbonyl-6'-cyclopentenylspectinomycin.

N,N'-dibenzyloxycarbonyl-6'-cyclohexylmethylspectinomycin.

CMR 202.0, 157.5, 138.0, 129.1, 178.3, 97.5, 92.3, 75.1, 74.7, 72.1, 67.2, 66.4, 65.6, 60.9, 60.7, 57.5, 57.3, 44.1, 38.2, 33.8, 33.5, 31.7, 31.4, 27.2, 26.9, ppm.

and the 6'-n-butylspectinomycin analogs of Tables XVII and XVIII.

N,N'-dibenzyloxycarbonyl-6'-undecylspectinomycin.

TABLE XVII

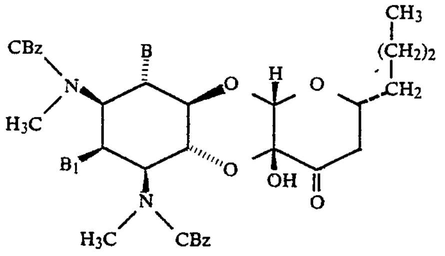

| B | $B_1$ |
|---|---|
| HO— | HO— |
| $CH_3O$— | HO— |
| $C_2H_5O$— | HO— |
| HS— | HO— |
| $CH_3S$— | HO— |
| $C_2H_5S$— | HO— |
| H— | HO— |
| HO— | H— |
| HO— | $CH_3O$— |
| HO— | $C_2H_5O$— |
| HO— | HS— |
| HO— | $CH_3S$— |
| HO— | $C_2H_5S$— |
| HO— | HO— |
| HO— | HO— |
| HO— | HO— |
| HO— | HO— |
| HO— | HO— |
| HO— | HO— |
| HO— | HO— |
| HO— | HO— |

TABLE XVIII

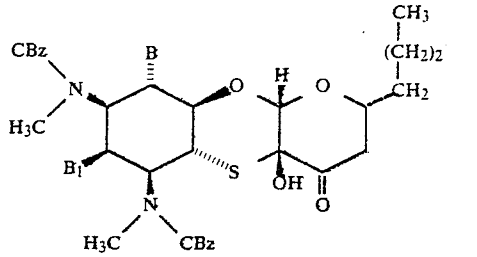

| B | $B_1$ | $R_{10}$ | $R_{11}$ |
|---|---|---|---|
| HO— | HO— | $CH_3\overset{\overset{O}{\parallel}}{C}-$ | $CH_3$— |
| $CH_3O$— | HO— | $CH_3\overset{\overset{O}{\parallel}}{C}-$ | $CH_3$— |
| $C_2H_5O$— | HO— | $CH_3\overset{\overset{O}{\parallel}}{C}-$ | $CH_3$— |
| HS— | HO— | $CH_3\overset{\overset{O}{\parallel}}{C}-$ | $CH_3$— |
| $CH_3S$— | HO— | $CH_3\overset{\overset{O}{\parallel}}{C}-$ | $CH_3$— |
| $C_2H_5S$— | HO— | $CH_3\overset{\overset{O}{\parallel}}{C}-$ | $CH_3$— |
| H— | HO— | $CH_3\overset{\overset{O}{\parallel}}{C}-$ | $CH_3$— |
| HO— | H— | $CH_3\overset{\overset{O}{\parallel}}{C}-$ | $CH_3$— |
| HO— | $CH_3O$— | $CH_3\overset{\overset{O}{\parallel}}{C}-$ | $CH_3$— |
| HO— | $C_2H_5C$— | $CH_3\overset{\overset{O}{\parallel}}{C}-$ | $CH_3$— |
| HO— | H— | $CH_3\overset{\overset{O}{\parallel}}{C}-$ | $CH_3$— |
| HO— | $CH_3S$— | $CH_3\overset{\overset{O}{\parallel}}{C}-$ | $CH_3$— |
| HO— | $\overset{\overset{O}{\parallel}}{C_2H_5S}-$ | $CH_3\overset{\overset{O}{\parallel}}{C}-$ | $CH_3$— |
| HO— | HO— | $C_2H_5\overset{\overset{O}{\parallel}}{C}-$ | $C_2H_5$— |
| HO— | HO— | $C_3H_7\overset{\overset{O}{\parallel}}{C}-$ | $C_3H_7$— |
| HO— | HO— | $C_4H_9\overset{\overset{O}{\parallel}}{C}-$ | $C_4H_9$— |
| HO— | HO— | $C_5H_{11}\overset{\overset{O}{\parallel}}{C}-$ | $C_5H_{11}$— |

TABLE XVIII-continued

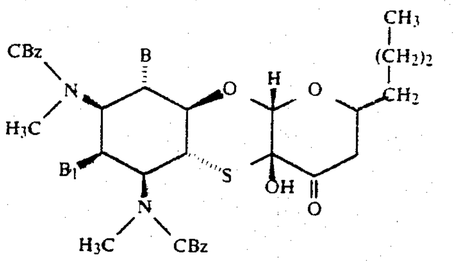

| B | $B_1$ | $R_{10}$ | $R_{11}$ |
|---|---|---|---|
| HO— | HO— | $C_6H_{13}\overset{O}{\overset{\|}{C}}$— | $C_6H_{13}$— |
| HO— | HO— | $C_7H_{15}\overset{O}{\overset{\|}{C}}$— | $C_7H_{15}$— |
| HO— | HO— | $C_8H_{17}\overset{O}{\overset{\|}{C}}$— | $C_8H_{17}$— |

EXAMPLE 1

6'-n-octylspectinomycin

N,N'-dibenzyloxycarbonyl-6'-n-octylspectinomycin (0.09 g) is dissolved in methanol (7.0 ml) and stirred under a nitrogen atmosphere. Palladium black (60 mg) is added followed by 97% formic acid (0.45 ml). After stirring well for 40 minutes the catalyst is filtered and the filtrate is concentrated at high vacuum. The residue is taken up in $H_2O$ (8 ml) and acidified to pH 1.5 with 0.1N hydrogen chloride (0.35 ml). The sample is freeze-dried to prepare a CMR sample. After CMR the sample was diluted with $H_2O$ and freeze-dried to give 0.05 g 6'-n-octylspectinomycin as its dihydrochloride.

CMR ($D_2O$, referenced to internal $CH_3CN$): 92.9, 92.6, 91.1, 70.9, 68.8, 65.1, 64.7, 60.6, 58.7, 57.5, 38.2, 33.4, 30.8, 30.1, 29.5, 28.5, 28.2, 24.2, 21.5, 12.8 ppm.

Utilizing a procedure similar to that used in Example 1 but substituting the appropriately substituted protected 6'-alkylspectinomycin for N,N'-dicarbobenzyloxy-6'n-octylspectinomycin, there is obtained as their dihydrochloride.

6'-ethylspectinomycin

CMR 29.8, 29.4, 60.6, 58.6, 57.6, 64.6, 70.7, 65.0, 92.7, 92.7, 91.0, 58.5, 68.8, 35.0, 16.6, 12.4 ppm.

6'-n-propylspectinomycin

CMR 29.8, 29.4, 60.6, 58.6, 57.6, 64.6, 70.9, 64.9, 92.6, 92.6, 91.0, 38.5, 68.7, 32.5, 25.4, 21.0, 12.3 ppm.

6'-n-butylspectinomycin

CMR 29.9, 24.4 60.4, 58.5, 57.4, 64.5, 70.7, 64.9, 92.5, 92.5, 90.9, 38.7, 68.7, 32.9, 30.1, 23.1, 20.4, 12.5 ppm.

6'-iso-butylspectinomycin

≢'-n-pentylspectinomycin

CMR 29.8, 29.3, 60.6, 58.6, 57.7, 64.7, 71.0, 65.0, 92.7, 92.7, 91.1, 38.6, 68.8, 32.9, 30.1, 23.2, 21.0, 20.8, 12.5 ppm.

6'-(3,3-dimethyl)-n-butylspectinomycin

6'-cyclopentylmethylspectinomycin

6'-cyclohexylmethylspectinomycin

CMR 30.1, 29.5, 60.6, 58.6, 57.5, 64.7, 70.9, 65.1, 92.6, 92.6, 91.1, 38.2, 68.8, 33.4, 30.7, 28.5, 28.5, 28.2, 28.2, 24.2, 21.5, 12.8 ppm.

6'-n-undecylspectinomycin

CMR 60.5, 58.6, 57.5, 64.9, 70.9, 65.2, 97.7, 92.8, 91.2, 38.8, 68.8, 33.4, 30.9, 28.4, 28.8, 28.8, 28.8, 28.8, 28.8, 28.8, 24.4, 21.5, 12.8, 30.2, 24.6 ppm.

and the 6'-n-octylspectinomycin analogs of Tables XIX and XX.

TABLE XIX

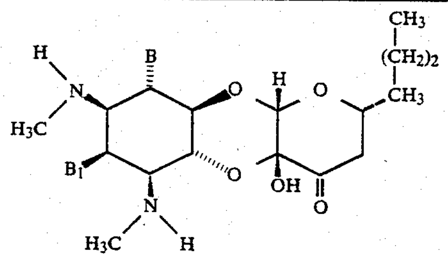

| B | $B_1$ |
|---|---|
| HO— | HO— |
| $CH_3O$— | HO— |
| $C_2H_5O$— | HO— |
| HS— | HO— |
| $CH_3S$— | HO— |
| $C_2H_5S$— | HO— |
| H— | HO— |
| HO— | H— |
| HO— | $CH_3O$— |
| HO— | $C_2H_5O$— |
| HO— | $H_2$— |
| HO— | $CH_3S$— |
| HO— | $C_2H_5S$— |

TABLE XX

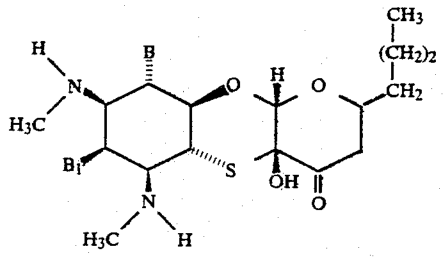

| B | $B_1$ |
|---|---|
| HO— | HO— |
| $CH_3O$— | HO— |
| $C_2H_5O$— | HO— |
| HS— | HO— |
| $CH_3S$— | HO— |
| $C_2H_5S$— | HO— |
| H— | HO— |
| HO— | H— |
| HO— | $CH_3O$— |
| HO— | $C_2H_5O$— |
| HO— | HS— |
| HO— | $CH_3S$— |
| HO— | $C_2H_5S$— |

EXAMPLE 2

6'-n-propylspectinomycin sulfate

N,N'-dibenzyloxycarbonyl-6'-n-octylspectinomycin (2.20 g) is dissolved in methanol (100 ml) and stirred under a nitrogen atmosphere. Palladium black (1.39 g) is added followed by 97% formic acid (4.3 ml). After stirring well the catalyst is filtered and the filtrate is concentrated at high vacuum. The residue is taken up in $H_2O$ (10 ml) and acidified with 1M aqueous hydrogen sulfate. (3.5 ml). The sample is freeze-dried and then recrystallized from acetone:water to give 0.87 g 6'-n-propylspectinomycin sulfate pentahydrate.

CMR ($D_2O$, referenced to internal $CH_3CN$): 118.07, 92.67, 91.24, 91.06, 70.73, 68.94, 65.01, 64.74, 60.78, 59.15, 57.69, 38.77, 32.83, 30.35, 29.77, 25.78, 21.18 and 12.45 ppm.

CHART A

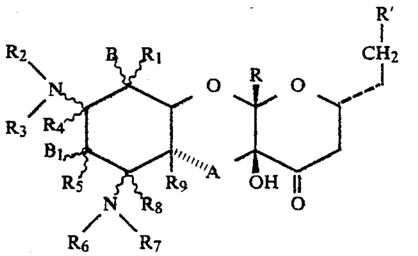
I

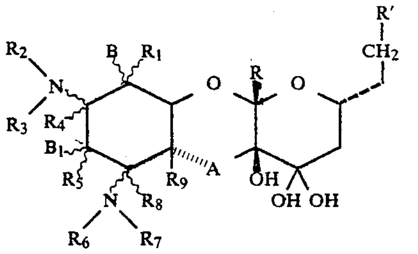
I'

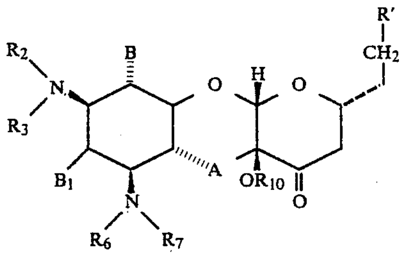
Ia

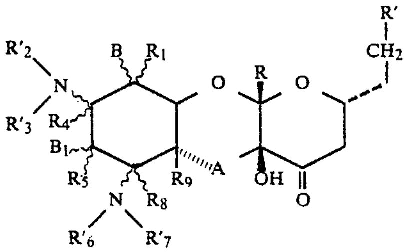
II

-continued

CHART A

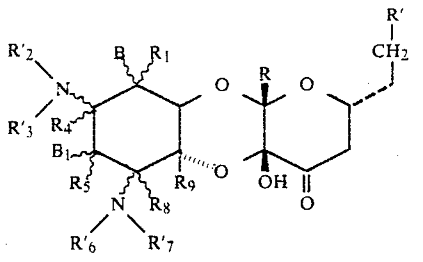
II'

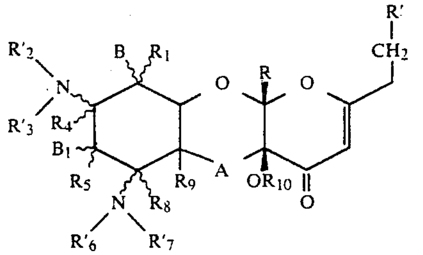
III

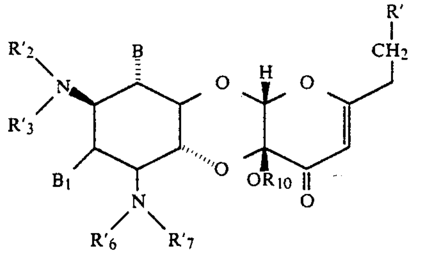
IIIa

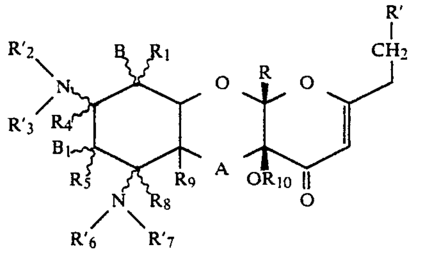
III'

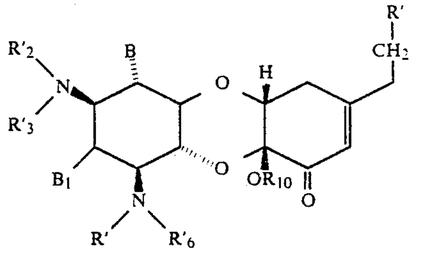
III'a

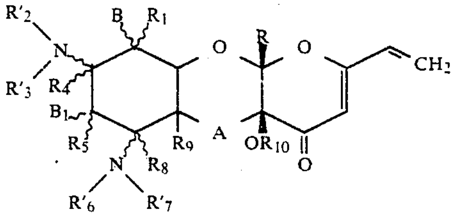
IV

-continued
CHART A
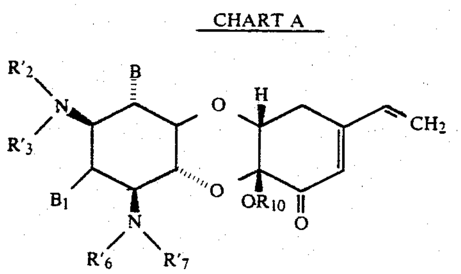
IVa
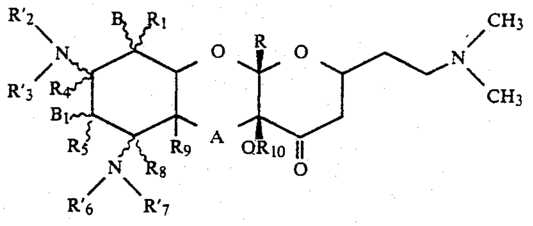
V
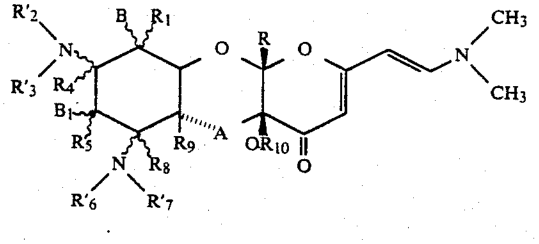
VI
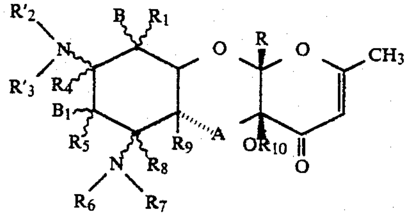
VII
Scheme 1
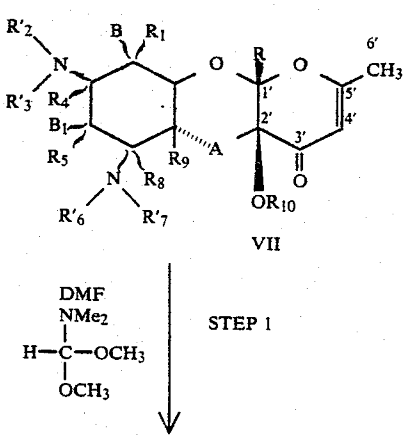
-continued
Scheme 1
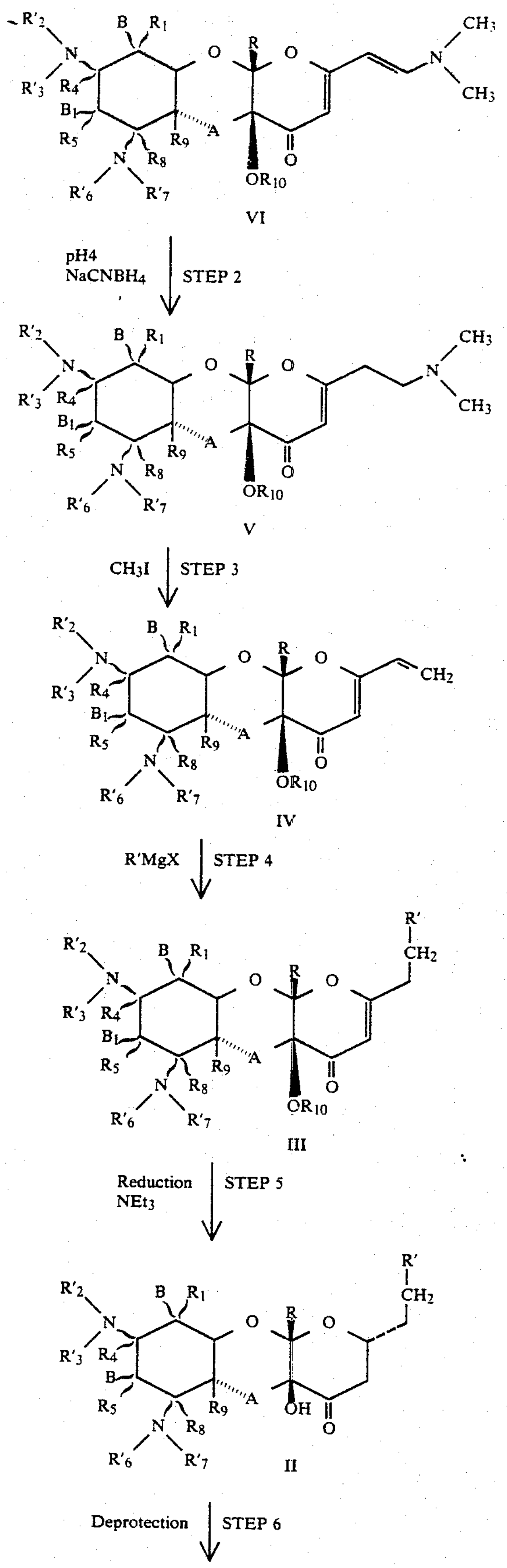

-continued

Scheme I

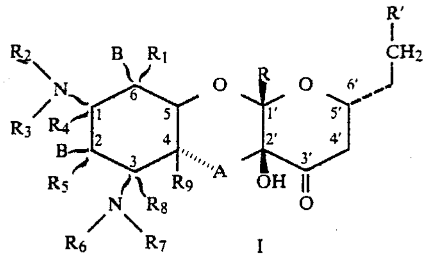

I

Scheme II

X

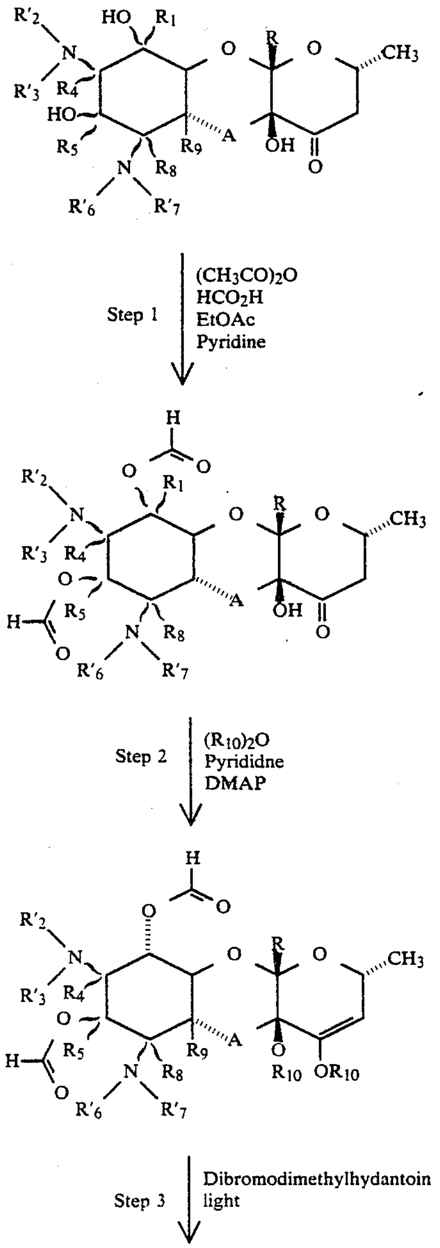

IX

VIII

-continued

Scheme II

VII

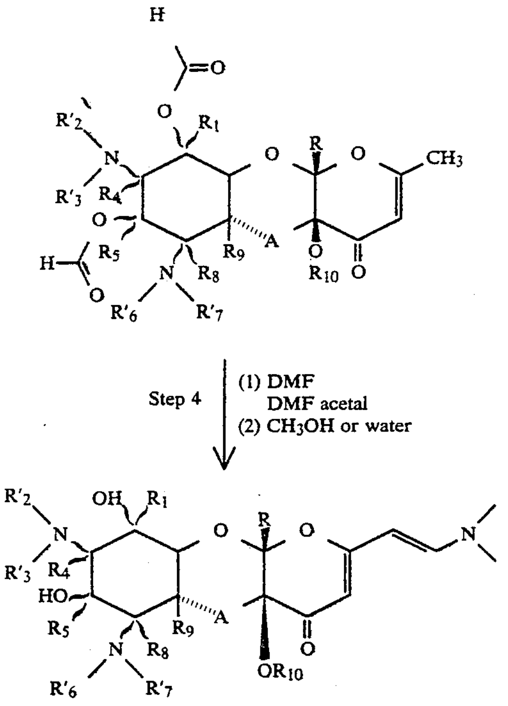

VI

I claim:

1. A compound having the formula

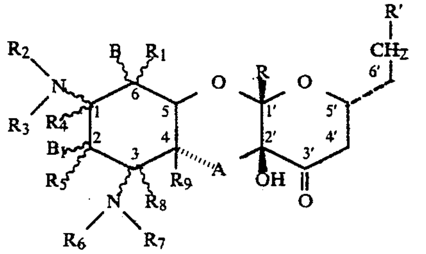

wherein R is hydrogen or lower alkyl; R' is selected from the group consisting of ethyl, n-propyl, n-butyl and an alkyl group cyclic or branch chain system, in which the longest extension of the branch or cyclic system contains from 1 to 4 carbon atoms, inclusive; $R_1$ through $R_9$ are selected from the group consisting of hydrogen, lower alkyl, lower alkenyl, and lower alkynyl; A is selected from the group consisting of oxygen and sulfur, and B and $B_1$ are the same or different and are selected from the group consisting of hydrogen, hydroxy, alkoxy, o-lower alkenyl, thio, thio-lower alkyl and thio-lower alkenyl, hydrated forms thereof, and pharmaceutically acceptable salts of the compound of formula I and hydrated forms thereof.

2. A compound according to claim 1 having the formula

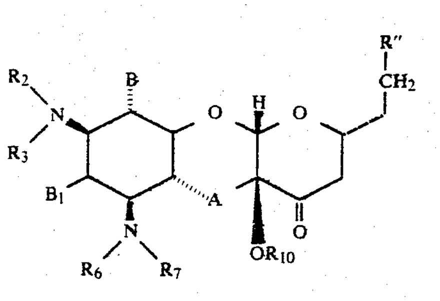

Ia wherein R" is selected from the group consisting of ethyl, n-propyl and n-butyl, $R_1$ through $R_9$ are selected from the group consisting of hydrogen, lower alkyl, lower alkenyl, and lower alkynyl; with the proviso that one of $R_2$ and $R_3$ is always hydrogen and one of $R_6$ and $R_7$ is always hydrogen; A is selected from the group consisting of oxygen and sulfur, and B and $B_1$ are the same or different and are selected from the group consisting of hydrogen, hydroxy, alkoxy, o-lower alkenyl, thio, thio-lower alkyl and thio-lower alkenyl; hydrated forms thereof, and pharmaceutically acceptable salts of the compound for formula I and hydrated forms thereof.

3. A compound according to claim 2, 6'-n-propylspectinomycin.

4. A compound according to claim 2, 6'-n-propylspectinomycin dihydrochloride.

5. A compound according to claim 2, 6'-n-propylspectinomycin sulphate.

6. A compound according to claim 2, 6'-n-butylspectinomycin.

7. A compound according to claim 2, 6'-n-butylspectinomycin dihydrochloride.

8. A compound according to claim 2, 6'-iso-butylspectinomycin.

9. A compound according to claim 2, 6'-iso-butylspectinomycin dihydrochloride.

10. A compound according to claim 2, 6'-n-pentylspectinomycin.

11. A compound according to claim 1, 6'-(3,3-dimethyl)-n-butyl-spectinomycin.

12. A compound according to claim 1, 6'-(3,3-dimethyl)-n-butyl-spectinomycin dihydrochloride.

13. A compound according to claim 1, 6'-cyclopentylmethylspectinomycin.

14. A compound according to claim 1, 6'-cyclopentylmethylspectinomycin dihydrochloride.

15. A compound according to claim 1, 6'-cyclohexylmethylspectinomycin.

16. A compound according to claim 1, 6'-cyclohexylmethylspectinomycin dihydrochloride.

17. The compound 6'-undecylspectinomycin.

18. The compound 6'-undecylspectinomycin dihydrochloride.

* * * * *

UNITED STATES PATENT OFFICE

CERTIFICATE OF CORRECTION

Patent No. 4,532,336 Dated 30 July 1985

Inventor(s) David R. White

It is certified that error appears in the above-identified patent and that said Letters Patent are hereby corrected as shown below:

Column 3, line 50: "etnyl" should read: -- ethyl --.

Column 12, line 5, Table V (Formula):

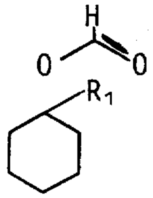

should read: --

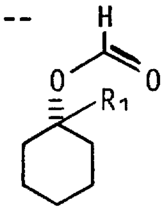

Column 16, line 47: "dimethyl acetyl acetal" should read: -- dimethyl acetal --.

Column 28, line 34: "acd" should read: -- acid --.

Column 31, line 65: "≠" should read: -- 6'- --.

Column 37, line 50: "Pyrididne" should read: Pyridine --.

Signed and Sealed this

Twenty-first Day of October, 1986

[SEAL]

*Attest:*

DONALD J. QUIGG

*Attesting Officer* *Commissioner of Patents and Trademarks*